US009782238B2

(12) United States Patent
Kopelman

(10) Patent No.: US 9,782,238 B2
(45) Date of Patent: Oct. 10, 2017

(54) METHODS, SYSTEMS AND ACCESSORIES USEFUL FOR PROCEDURES RELATING TO DENTAL IMPLANTS

(71) Applicant: ALIGN TECHNOLOGY, INC., San Jose, CA (US)

(72) Inventor: Avi Kopelman, Palo Alto, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

(21) Appl. No.: 15/138,034

(22) Filed: Apr. 25, 2016

(65) Prior Publication Data

US 2016/0235506 A1 Aug. 18, 2016

Related U.S. Application Data

(62) Division of application No. 13/960,599, filed on Aug. 6, 2013, now Pat. No. 9,345,562, which is a division
(Continued)

(51) Int. Cl.
*A61C 11/00* (2006.01)
*A61C 8/00* (2006.01)
(Continued)

(52) U.S. Cl.
CPC .............. *A61C 8/00* (2013.01); *A61C 8/0001* (2013.01); *A61C 9/00* (2013.01); *A61C 9/0053* (2013.01);
(Continued)

(58) Field of Classification Search
CPC ......... A61C 8/0001; A61C 19/05; A61C 9/00; A61C 13/0004; A61C 8/00; A61C 9/0053; A61C 13/0022; A61C 13/34; A61C 9/002
See application file for complete search history.

(56) References Cited

U.S. PATENT DOCUMENTS 2,467,432 A 4/1949 Kesling
3,407,500 A 10/1968 Kesling
(Continued)

FOREIGN PATENT DOCUMENTS

AU 3031677 A 5/1979
AU 517102 B2 7/1981
(Continued)

OTHER PUBLICATIONS

European search report dated Jun. 30, 2016 for EP Application No. 16164374.
(Continued)

*Primary Examiner* — Heidi M Eide
(74) *Attorney, Agent, or Firm* — Wilson Sonsini Goodrich & Rosati

(57) ABSTRACT

A method and system are provided for manufacturing a physical dental model. A virtual model is provided representative of at least a portion of the intra-oral cavity including at least one dental implant implanted therein, and the virtual model includes a virtual portion representative of each dental implant. The virtual spatial disposition of each such virtual portion is determined with respect to the virtual model, corresponding to a real spatial disposition of the respective implant with respect to the intra oral cavity. A physical model is then manufactured based on the virtual model, the physical model including a physical analog corresponding to each implant at a respective physical spatial disposition with respect to the physical model corresponding to the respective virtual spatial disposition of the respective virtual portion with respect to the first virtual model as already determined. In some embodiments, a jig is provided configured for maintaining a desired physical spatial disposition between the physical analog and a cavity
(Continued)

of the physical dental model at least until the physical analog is affixed in the cavity.

10 Claims, 15 Drawing Sheets

Related U.S. Application Data of application No. 12/458,579, filed on Jul. 16, 2009, now Pat. No. 8,509,932.

(60) Provisional application No. 61/129,770, filed on Jul. 17, 2008.

(51) Int. Cl.
    *A61C 9/00*         (2006.01)
    *A61C 13/00*       (2006.01)
    *A61C 13/34*       (2006.01)

(52) U.S. Cl.
    CPC ...... *A61C 13/0004* (2013.01); *A61C 13/0022* (2013.01); *A61C 13/34* (2013.01); *A61C 9/002* (2013.01)

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,240,605 A | 12/1980 | Waltke et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |

(56) References Cited

U.S. PATENT DOCUMENTS

| | | | |
|---|---|---|---|
| 6,062,861 A | 5/2000 | Andersson |
| 6,068,482 A | 5/2000 | Snow |
| 6,099,313 A | 8/2000 | Dorken et al. |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,358,052 B1 | 3/2002 | Lustig et al. |
| 6,382,975 B1 | 5/2002 | Poirier |
| 6,398,548 B1 | 6/2002 | Muhammad et al. |
| 6,402,707 B1 | 6/2002 | Ernst |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 7,018,207 B2 | 3/2006 | Prestipino |
| 7,731,497 B2 | 6/2010 | De Moyer |
| 7,774,084 B2 | 8/2010 | Cinader |
| 8,011,925 B2 | 9/2011 | Powell et al. |
| 8,257,083 B2 | 9/2012 | Berckmans et al. |
| 8,509,932 B2 | 8/2013 | Kopelman |
| 9,345,562 B2 | 5/2016 | Kopelman |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer |
| 2004/0126731 A1 | 7/2004 | Tucker et al. |
| 2004/0128010 A1 | 7/2004 | Pavlovskaia et al. |
| 2005/0055118 A1 | 3/2005 | Nikolskiy et al. |
| 2006/0183078 A1 | 8/2006 | Niznick |
| 2006/0281041 A1 | 12/2006 | Rubbert et al. |
| 2007/0015111 A1* | 1/2007 | Kopelman ......... A61C 13/0004 433/213 |
| 2007/0092854 A1 | 4/2007 | Powell et al. |
| 2007/0224576 A1* | 9/2007 | Ihde .................... A61C 8/0001 433/173 |
| 2008/0032262 A1 | 2/2008 | Bondar |
| 2008/0032263 A1 | 2/2008 | Bondar |
| 2008/0153067 A1 | 6/2008 | Berckmans et al. |
| 2008/0176187 A1 | 7/2008 | Stumpel |
| 2009/0220916 A1 | 9/2009 | Fisker et al. |
| 2010/0021859 A1 | 1/2010 | Kopelman |
| 2010/0105008 A1 | 4/2010 | Powell et al. |
| 2010/0260405 A1 | 10/2010 | Cinader |
| 2011/0004331 A1 | 1/2011 | Cinader et al. |
| 2011/0066267 A1 | 3/2011 | Schmitt |
| 2011/0129792 A1 | 6/2011 | Berckmans et al. |
| 2011/0200970 A1 | 8/2011 | Berckmans et al. |
| 2014/0038135 A1 | 2/2014 | Kopleman |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| DE | 20309508 U | 10/2003 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| EP | 1172072 A1 | 1/2002 |
| ES | 463897 | 1/1980 |
| FR | 2369828 A1 | 6/1978 |
| FR | 2652256 A1 | 3/1991 |
| GB | 1550777 A | 8/1979 |
| GB | 15500777 | 8/1979 |
| JP | 53-058191 | 5/1978 |
| JP | 04-028359 | 1/1992 |
| JP | 08-508174 | 9/1996 |
| JP | H08508174 A | 9/1996 |
| TW | I224961 B | 12/2004 |
| TW | M348588 U | 1/2009 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO 00/08415 A1 | 2/2000 |
| WO | WO 2007/005490 * | 1/2007 ............... A61C 5/10 |

OTHER PUBLICATIONS

AADR. American Association for Dental Research, Summary of Activities, Mar. 20-23, 1980, Los Angeles, CA, p. 195.

Alcaniz, et al. "An Advanced System for the Simulation and Planning of Orthodontic Treatments," Karl HF Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures, " AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

(56) References Cited

OTHER PUBLICATIONS

Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive,Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/-pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays. In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121- 133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision- Literally," "Part 4: Bytes 'N Bites" The Computer Moves From the Front Desk to the Operatoiy, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin Orthod., 7(4):258-265 (Dec. 2001).

Cutting et al., "Three-Dimensional Computer-Assisted Design of Craniofacial Surgical Procedures: Optimization and Interaction with Cephalometric and Ct-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992).
Definition for gingiva. Dictionary.com p. 1-3. Retrieved from the internet Nov. 5, 2004 <http://reference.com/search/search?q=gingiva>.
DeFranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations. State of the Art of the CEREC-Method, May 1991, 2 pages total.
Dentrac Corporation, Dentrac document, pp. 4-13 (1992).
DENT-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
European search report Jul. 7, 2010 for EP Application No. 091801970.
Faber et al., "Computerized Interactive Orthodontic Treatment Planning," Am. J. Orthod., 73(1):36-46 (Jan. 1978).
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et al., "Automated Finite Element Modeling of a Human Mandible with Dental Implants," JS WSCG '98 -Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et al., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputon-fa . . . >.

(56) References Cited

OTHER PUBLICATIONS

Hikage, "Integrated Orthodontic Management System for Virtual Three-Dimensional Computer Graphic Simulation and Optical Video Image Database for Diagnosis and Treatment Planning", Journal of Japan Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays. Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginate Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays. Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System" Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).

(56) References Cited

OTHER PUBLICATIONS

Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances-Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee Orthodontic Appliances-Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20,1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances-Pro Lab product information for patients, 2 pages (2002).

\* cited by examiner

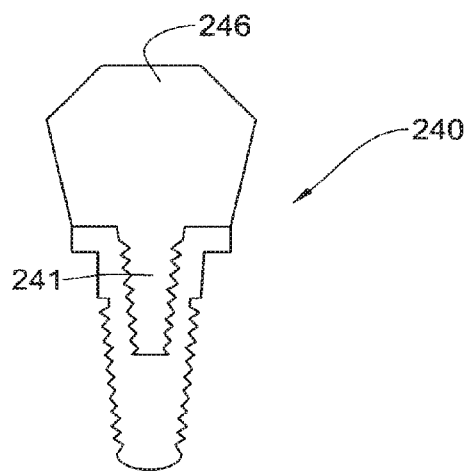
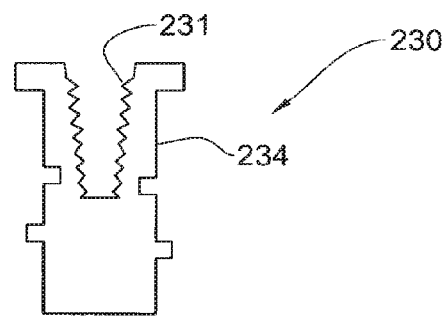
FIG. 3(a)　　　　　　　　FIG. 3(b)
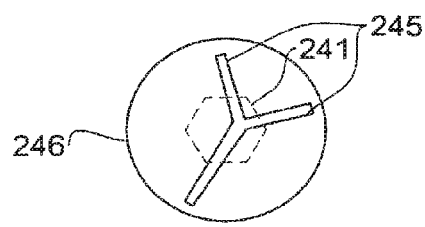
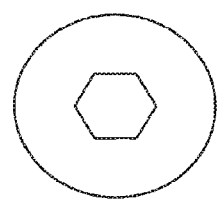
FIG. 3(c)　　　　　　　　FIG. 3(d)

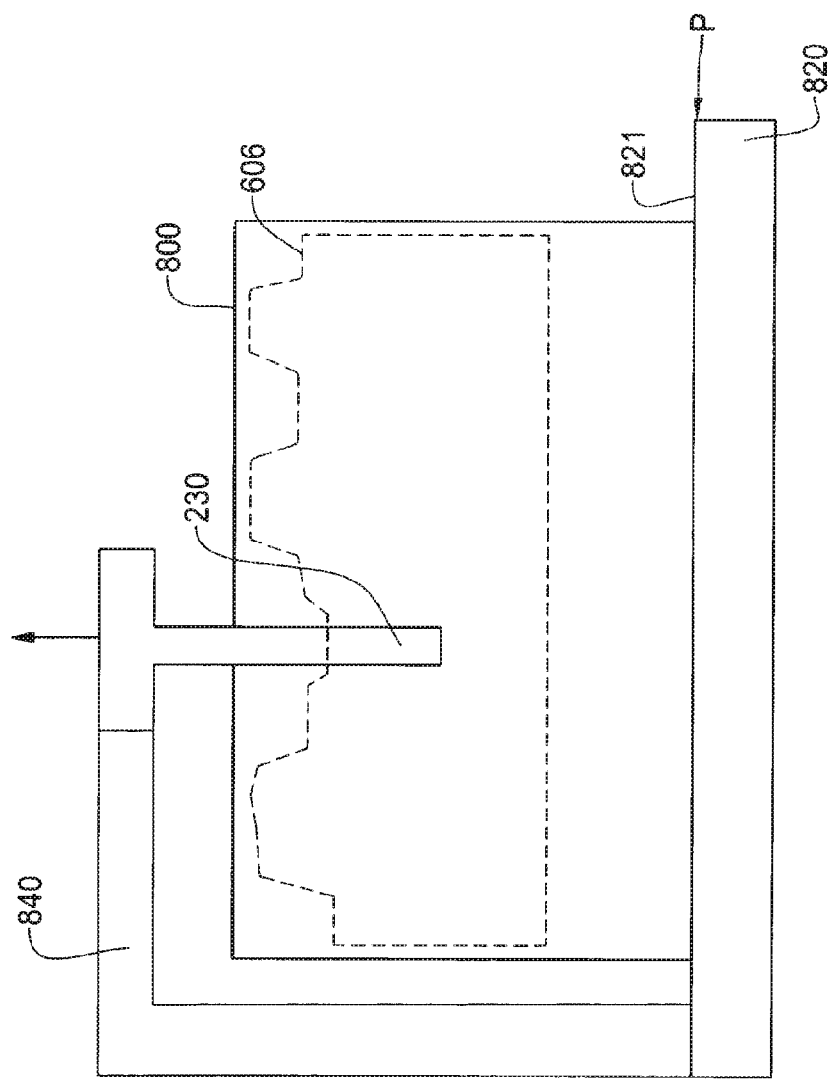

METHODS, SYSTEMS AND ACCESSORIES USEFUL FOR PROCEDURES RELATING TO DENTAL IMPLANTS

CROSS-REFERENCE

This application is a divisional of U.S. patent application Ser. No. 13/960,599, filed Aug. 6, 2013, now U.S. Pat. No. 9,345,562, issued May 24, 2016, which is a divisional of U.S. patent application Ser. No. 12/458,579, filed Jul. 16, 2009, now U.S. Pat. No. 8,509,932, issued Aug. 13, 2013, which claims the benefit of U.S. Provisional Patent Application No. 61/129,770, filed Jul. 17, 2008, the contents of each of which are hereby incorporated by reference in their entirety.

FILED OF THE INVENTION

This invention relates to dental implants, in particular to methods, systems and accessories useful in procedures relating to dental implants.

BACKGROUND OF THE INVENTION

Dental implants are widely used as artificial substitutes for the root portion of missing teeth, and allow a tooth prosthesis to be securely anchored to the jaw via a permanent abutment mounted to the implant. Endosseous implants generally comprise an externally threaded body, often self-taping into the bone tissues, and further comprise an internal chamber that is configured, typically internally threaded, for receiving and securing therein the anchoring stem of a permanent abutment therein.

Following implantation of an implant in the intra oral cavity and healing of the surrounding tissues, a physical model of the intra oral cavity is produced for facilitating design and manufacture of the permanent abutment and prosthesis or other restoration that is to be eventually mounted onto the implant. In one procedure, an impression abutment is mounted to the implant so that it projects into the intra oral cavity, and an impression is then obtained of the intraoral cavity using well known techniques and impression materials, for example PVS. The impression abutment may be of the pick-up type, to be embedded with the impression material and retained therein after the impression tray is removed. Alternatively the impression tray is removed without the impression abutment attached thereto, but nevertheless having a recess formed therein complementary to the outer shape of the impression abutment, enabling the transfer-type impression abutment to be mounted therein at a later time. Subsequently an analog, corresponding to the particular implant that is implanted in the patient, is attached to the abutment, which is in situ in the impression material, and plaster is poured into the impression tray including the analog to produce a positive plaster model of the intraoral cavity with the analog embedded. The analog, in particular the internal passage thereof which is substantially identical to the internal passage of the implant that is designed to receive, engage and secure the permanent abutment, is in a position and orientation in the plaster model corresponding to the position and orientation of the implant in the patient's intra oral cavity. The dental technician can now attach a permanent abutment, or custom design a permanent abutment to fit the implant, build a coping or bridge framework or prosthesis to fit into the intraoral cavity of the patient.

By way of general background, the following publications relate to implants:

U.S. Pat. No. 6,358,052 discloses a dental implant system and method for effecting a dental restoration using the same. The dental implant system having an implant fixture adapted to be deployed in a bone; an impression coping adapted to be selectively deployed on the implant fixture and in a dental impression; a laboratory analog adapted to be selectively deployed on the impression coping and in a dental cast; a spherical abutment adapted to be selectively deployed on the laboratory analog; and a multiaxis abutment adapted to be adjustably deployed on the spherical abutment; wherein the spherical abutment and the multiaxis abutment are used to generate a cast permanent abutment which may be received by the laboratory analog and the implant fixture.

US 2008/032262 discloses a dental implant system comprising an implant member, an abutment member and a transfer key with cooperatively engaging structures for ensuring proper alignment and orientation of an abutment assembled on the implant member and for preparing an accurate dental impression and mold which represents the implantation site and its relationship to adjacent teeth structures. A dental reconstruction method utilizing the dental implant system of the present invention is also disclosed.

US 2006/183078 discloses a one-piece, screw-receiving, externally-threaded endosseous dental implant that includes a body portion with external threading and, at its proximal end, an unthreaded, cylindrical portion including a retentive groove for engaging a complementary transfer component or comfort cap; a one- or two-piece screw-receiving implant abutment for attachment to a one or two-piece implant, including a retentive groove for engaging a complementary transfer component or comfort cap; and a fixture mount for insertion in a one-piece implant, that can be sectioned with the distal end used to extend the implant height.

SUMMARY OF THE INVENTION

The term virtual model is used herein synonymously with "numerical entity", "3D model", and other such terms, and relates to a virtual representation in a computer environment of a real object, for example a dentition or at least a part of intraoral cavity, or of a real model thereof, for example.

The term "scanning" refer to any procedure directed at obtaining 3D topographic data of a surface, particularly of a dental surface, and thus includes mechanical methods, typically based on 3D probes for example, optical methods, including for example confocal methods, for example as disclosed in WO 00/08415, the contents of which are incorporated herein in their entirety by reference, or indeed any other method.

The term "display" refer to any means or method for delivering a presentation, which may include any information, data, images, sounds, etc, and thus the delivery may be in visual and/or audio form.

According to a first aspect of the invention, there is provided a method and system for manufacturing a physical dental model. A virtual model is provided representative of at least a portion of the intra-oral cavity including at least one dental implant implanted therein, and the virtual model includes a virtual portion representative of each dental implant. The virtual spatial disposition of each such virtual portion is determined with respect to the virtual model, corresponding to a real spatial disposition of the respective implant with respect to the intra oral cavity. A physical model is then manufactured based on the virtual model, the physical model including a physical analog corresponding to each implant at a respective physical spatial disposition with respect to the physical model corresponding to the respective virtual spatial disposition of the respective virtual portion with respect to the first virtual model as already determined.

In some embodiments, a jig is provided configured for maintaining a desired physical spatial disposition between the physical analog and a cavity of the physical dental model at least until the physical analog is affixed in the cavity.

According to this aspect of the invention, there is provided a method for manufacturing a physical dental model, comprising (a) providing a first virtual model representative of at least a portion of the intraoral cavity including at least one dental implant implanted therein, said first virtual model comprising a virtual portion representative of the or each said dental implant;

(b) determining a virtual spatial disposition of the or each said virtual portion with respect to the first virtual model corresponding to a real spatial disposition of the respective said implant with respect to said portion of the intra oral cavity; and (c) manufacturing a physical model of said portion of the intra-oral cavity based on said first virtual model, said physical model including a physical analog corresponding to the or each said implant at a respective physical spatial disposition with respect to said physical model corresponding to the respective said virtual spatial disposition of said virtual portion with respect to the first virtual model based on said determination in step (b).

The first virtual model may be generated in any suitable manner—for example by scanning the intraoral cavity in vivo, or scanning a positive or negative physical model of the intraoral cavity that includes representations of the implant(s) and a part of the dentition in the vicinity the implant(s).

In at least some embodiments, step (b) comprises providing a second virtual model at least partially representative of the or each respective said physical analog, and incorporating said second virtual model with said first virtual model based on said determination of the respective said virtual spatial disposition, to generate a third virtual model, wherein in step (c), said manufacturing of said physical model is based on said third virtual model. For example, step (b) may comprise manipulating the or each said second virtual model into an aligned spatial disposition with respect to the respective said virtual spatial disposition, and generating said third virtual model based on the first virtual model and including a virtual cavity (i.e. a virtual representation of the cavity) for virtually receiving and accommodating the or each respective second virtual model therein in a manner corresponding to that required for the respective physical analog with respect to said physical model of the intra oral cavity.

Step (c) may comprise forming an outer model surface corresponding to dental surfaces of said portion of the intra oral cavity, and forming a recess in said physical model (corresponding to the virtual cavity) for accommodating a respective said analog at the respective said physical spatial disposition, said recess corresponding to the respective said virtual cavity.

In at least some embodiments, at least one said virtual cavity is generated having a form generally complementary to that of the respective said physical analog, such that the respective said recess formed in said physical model provides a friction fit with respect to the respective said physical analog to accommodate the respective said physical analog at the respective said physical spatial disposition.

In at least some other embodiments, at least one said virtual cavity is generated having a form generally complementary to that of the respective said physical analog including a jacket, such that the respective said recess formed in said physical model provides a significant clearance gap with respect to the respective said physical analog, wherein said respective physical analog comprises said jacket formed of suitable model material, said jacket having an external form substantially complementary to that of the respective said recess, to enable the respective physical analog including the respective jacket to be accommodated in the respective said recess at the respective said physical spatial disposition. The said external form for the respective said jacket may be configured for fixing the spatial disposition thereof in the respective said recess in six degrees of freedom. For example, the jacket may be formed by a casting process applied to the respective said physical analog, or by applying a layer of said model material on the respective physical analog, and CNC machining said layer to provide the respective said external form.

In at least some embodiments, at least one said virtual cavity is generated having a form generally complementary to that of the respective said physical analog, such that the respective said recess formed in said physical model provides a significant clearance gap with respect to the respective said physical analog, wherein a suitable filler material is applied to fill the clearance gap, to enable the respective physical analog including the respective jacket to be accommodated in the respective said recess at the respective said physical spatial disposition. For example, the filler material may comprise a suitable cementing material. A suitable jig may be used for maintaining a said physical spatial disposition between the respective physical analog and the respective cavity at least until the physical analog is affixed therein by means of the filler material. In at least some embodiments, the jig may comprise a base, that is mounted in fixed spatial relationship to the physical dental model, for example affixed to a portion of the physical model, at least until the physical analog is affixed therein. In at least some embodiments, said portion of the physical model does not include physical model representations of teeth adjacent to a said implant.

In at least some embodiments, step (c) comprises forming an outer model surface corresponding to dental surfaces of said portion of the intra oral cavity from a blank of model material, wherein said blank integrally includes the or each said physical analog in relative spatial dispositions to one another corresponding to the relative spatial dispositions of the or each dental implants with respect to one another in said portion of the intra oral cavity.

In at least some embodiments, step (d) comprises computer controlled manufacture of at least a portion of said physical model. For example, step (d) may comprise manufacturing said physical model via a material removal operation applied to a blank of material or a rapid prototyping process.

According to this aspect of the invention, there is also provided a dental model, manufactured according to the above method.

According to at least some embodiments, a physical model is manufactured with a hole for friction fit with the analog.

According to at least some other embodiments, the analog is embedded in a suitable material, which is milled for a close fit with the hole, which may be useful, for example, when the analog is of a shape that does not allow friction fitting.

According to at least some other embodiments, the model is manufactured with a relatively large cavity such as to provide a loose fit for the analog, which is cemented in place while held in a jig.

According to another embodiment, a plaster blank is cast with the analog embedded in a particular known position. The blank is then machined to ensure that the analogue is in the correct position/orientation with the other parts (e.g., model dental surfaces) of the finished physical model.

According to this aspect of the invention, there is also provided a system for manufacturing a physical dental model of an intra-oral cavity, comprising:

(A) scanning apparatus and computer system configured for providing a first virtual model representative of at least a portion of the intra-oral cavity including at least one dental implant implanted therein, said first virtual model comprising a virtual portion representative of the or each said dental implant, and for determining a virtual spatial disposition of the or each said virtual portion with respect to the first virtual model corresponding to a real spatial disposition of the respective said implant with respect to the intra oral cavity;

(B) a physical analog corresponding to the or each said implant;

(C) a manufacturing system for manufacturing a physical model of said portion of the infra-oral cavity based on said first virtual model, said physical model including a physical analog corresponding to the or each said implant at a respective physical spatial disposition with respect to said physical model corresponding to the respective said virtual spatial as determined by said computer system.

The manufacturing system is computer controlled. For example, the manufacturing system may be configured for manufacturing said physical model via a material removal operation applied to a blank of material, or via a rapid prototyping technique.

According to another aspect of the invention, there is also provided accessories including one or more of a physical tooth model and a jig.

In one embodiment, a jig is provided for maintaining a desired spatial disposition between a respective analog and the respective cavity of a physical model of an intra oral cavity at least until the analog is affixed therein, wherein the jig comprises a base configured for being mounted to a portion of the physical model not including portions representative of adjacent teeth with respect to an implant site.

According to another aspect of the invention, there is provided a method for modifying a physical dental model, comprising:

(A) providing a physical model representative of at least a portion of the intra-oral cavity including at least one dental implant implanted therein, said physical model comprising a model portion representative of the or each said dental implant;

(B) providing a first virtual model representative of at least a portion of the intra-oral cavity including at least one dental implant implanted therein, said first virtual model comprising a virtual portion representative of the or each said dental implant;

(C) determining a virtual spatial disposition of the or each said virtual portion with respect to the first virtual model corresponding to a real spatial disposition of
the respective said implant with respect to said portion of the intra oral cavity; and •

(D) modifying said physical model of said portion of the intra-oral cavity by including therein a physical analog corresponding to the or each said implant at a respective physical spatial disposition with respect to said physical model corresponding to the respective said virtual spatial disposition of said virtual portion with respect to the first virtual model based on said determination in step (C).

The method according to this aspect of the invention may comprise one or more of the elements and features as provided herein regarding the first aspect of the invention, mutatis mutandis.

According to another aspect of the invention there is provided an accessory in the form of a jig configured for maintaining a desired physical spatial disposition between a physical analog and a cavity of a physical dental model at least until the physical analog is affixed in said cavity.

The cavity is typically larger (wider and/or deeper than the the part of the analog that needs to be embedded in the physical model providing a fellable clearance gap therebetween, and the analog is ultimately secured in the cavity via a suitable filler material, for example.

According to at least some embodiments, the jig may comprise a strut having a first end configured for being mounted with respect to the dental model at a first spatial disposition with respect thereto, and a second end configured for enabling the physical analog to mounted to the second end at a second spatial disposition with respect thereto, wherein said first end is at a third spatial disposition with respect to said second end, and wherein said first spatial disposition, said second spatial disposition and said third spatial disposition are chosen to provide said desired physical spatial disposition between the physical analog and the cavity when said strut is mounted with respect to the dental model and the physical analog is mounted to said strut.

In at least some embodiments, the jig may comprise a spacer member, wherein said strut comprises an elongate arm comprising said first end and said second end at opposed longitudinal ends of said elongate arm, wherein said first end comprises a strut base portion configured for being mounted to the dental model via said spacer member wherein to provide said first spatial disposition between said first end and the dental model.

Said strut base portion may be configured for enabling said spacer member to be mounted to said strut by engagement to the strut base portion. At least one of the strut base portion and said spacer member may comprise a first engagement arrangement to ensure that the spacer member may be mounted to the strut base portion in a spatial disposition with respect thereto that is fixed in six degrees of freedom. For example, the first engagement arrangement may comprise at least two laterally spaced pins projecting from a second spacer end of said spacer member and corresponding complementary wells formed in the strut base portion for receiving each said pin. Other alternative configurations for the first engagement arrangement may of course be provided.

The dental model may include a model base portion configured for enabling said spacer member to be mounted to the dental model by engagement to the model base portion. At least one of the model base portion and said spacer member may comprise a second engagement arrangement to ensure that the spacer may be mounted to the model base portion in a spatial disposition with respect thereto that is fixed in six degrees of freedom. For example, said second engagement arrangement may comprise at least two laterally spaced pins projecting from a first spacer end of said spacer member and corresponding complementary wells formed in the model base portion for receiving each said pin. Other alternative configurations for the second engagement arrangement may of course be provided.

In at least some embodiments, said spacer comprises a first spacer end and a second spacer end, wherein said first spacer end is configured for being mounted to said first end via said strut base portion in a spatial disposition with respect thereto that is fixed in six degrees of freedom, and wherein said second spacer end is configured for being mounted to the dental model via a model base portion of the dental model in a spatial disposition with respect to the model base portion that is fixed in six degrees of freedom.

The geometric form of the jig, in particular the specific spatial dispositions of the various parts thereof to properly mate with the physical dental model, can be based on the method provided according to the first aspect of the invention.

For example, the jig may be integrally produced from a suitable blank via a material removal operation or integrally produced via a suitable rapid prototyping operation, based on the geometric form previously determined.

According to this aspect of the invention there is also provided a jig particularly useful for dental implant procedures, comprising:

an arm having a first arm end and a second arm end spaced from said first arm end, said first arm end having a first engagement arrangement, and said second arm end being configured for releasably holding a physical analog;

a spacer element having a first spacer end and a second spacer end spaced from said first spacer end, said first spacer end being configured for engagement to said first arm end via said first engagement arrangement, and said second spacer end being configured for being mounted to a physical dental model representative of at least a portion of the real dentition of a patient, said dental model comprising a cavity wherein in operation to maintain a desired physical spatial disposition between the physical analog and said cavity of the physical dental model, wherein the physical analog is at least partially received within the cavity, at least until the physical analog is affixed in said cavity.

As for other embodiments of the jig, said desired physical spatial disposition of the physical analog with respect to the dental model corresponds to a spatial disposition of a dental implant corresponding to the analog with respect to the real dentition that is being represented by the dental model.

According to this aspect of the invention there is also provided a kit particularly useful for dental implant procedures, comprising:

a physical dental model comprising a model dentition representative of a first real dentition of a patient, and further comprising a cavity configured for accommodating therein via a fellable gap a physical analog in a model spatial disposition with respect to said model dentition corresponding to a real spatial disposition of an implant with respect to said real dentition;

a jig configured for holding said physical analog in said model spatial disposition with respect to said cavity at least until the physical analog is affixed in said cavity.

In at least some embodiments, the jig may comprise a spacer member and a strut, said strut comprising a strut base portion configured for being mounted to said dental model via said spacer member, and a strut end configured for holding the physical analog thereat.

The dental model may comprise a model base portion configured for enabling said spacer member to be mounted to the dental model by engagement to the model base portion.

The spacer may comprise a first spacer end and a second spacer end, wherein said first spacer end is configured for being mounted to said strut via said strut base portion in a spatial disposition with respect thereto that is fixed in six degrees of freedom, and wherein said second spacer end is configured for being mounted to the dental model via said model base portion of the dental model in a spatial disposition with respect to the model base portion that is fixed in six degrees of freedom.

The model dentition is generally representative of a set of adjacent real teeth of a first dental arch of a patient, and may comprise a set of model teeth corresponding to a set of real teeth of at least a portion of a first dental arch of a patient, and wherein said cavity is located adjacent at least one said model tooth at a position corresponding to a missing tooth in the real dentition.

The kit may optionally further comprise an auxiliary dental model representative of a second real dentition of at least a portion of a second dental arch of the patient, wherein the second real dentition is occlusally opposed with respect to the first real dentition. The auxiliary dental model may be configured for being mounted with respect to said dental model in an occlusal relationship corresponding to that between said first real dentition and said second real dentition. This may be accomplished by mounting the two models to the spacer, or to a suitable articulator, for example.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 3(a) and FIG. 3(c) illustrate in side view and top view, respectively, an implant and impression abutment according to an embodiment of the invention; FIG. 3(b) and FIG. 3(d) illustrate in side view and top view, respectively, an analog corresponding to the implant of FIG. 3(a) and FIG. 3(c).

FIG. 15 illustrates in side view a blank for manufacturing a physical model according to a fourth embodiment of the invention.

DETAILED DESCRIPTION OF THE INVENTION

According to one aspect of the present invention there is provided a system and method for use in dental implant procedures.

Figure 1:
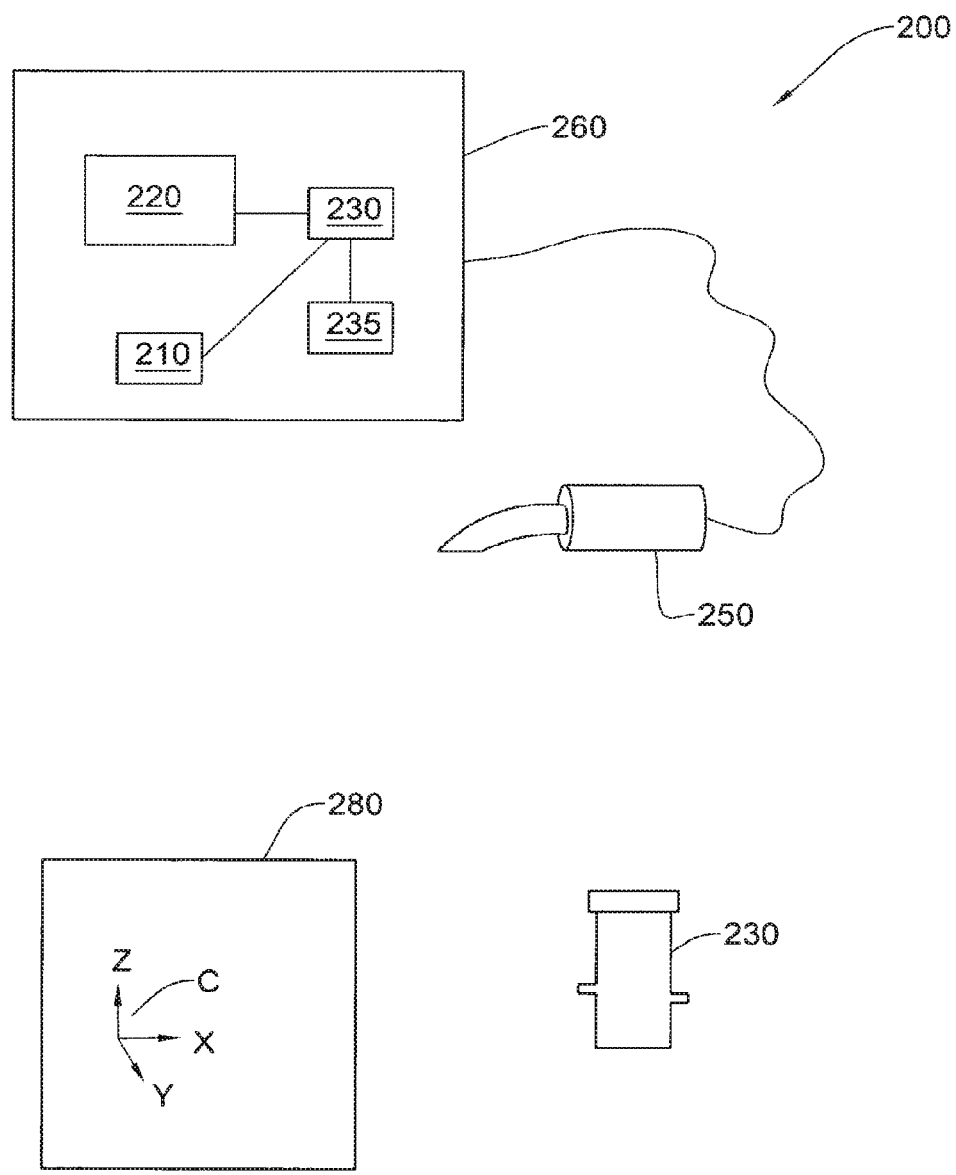
FIG. 1 is a schematic illustration of a system according to an embodiment of the invention.
Figure 2:
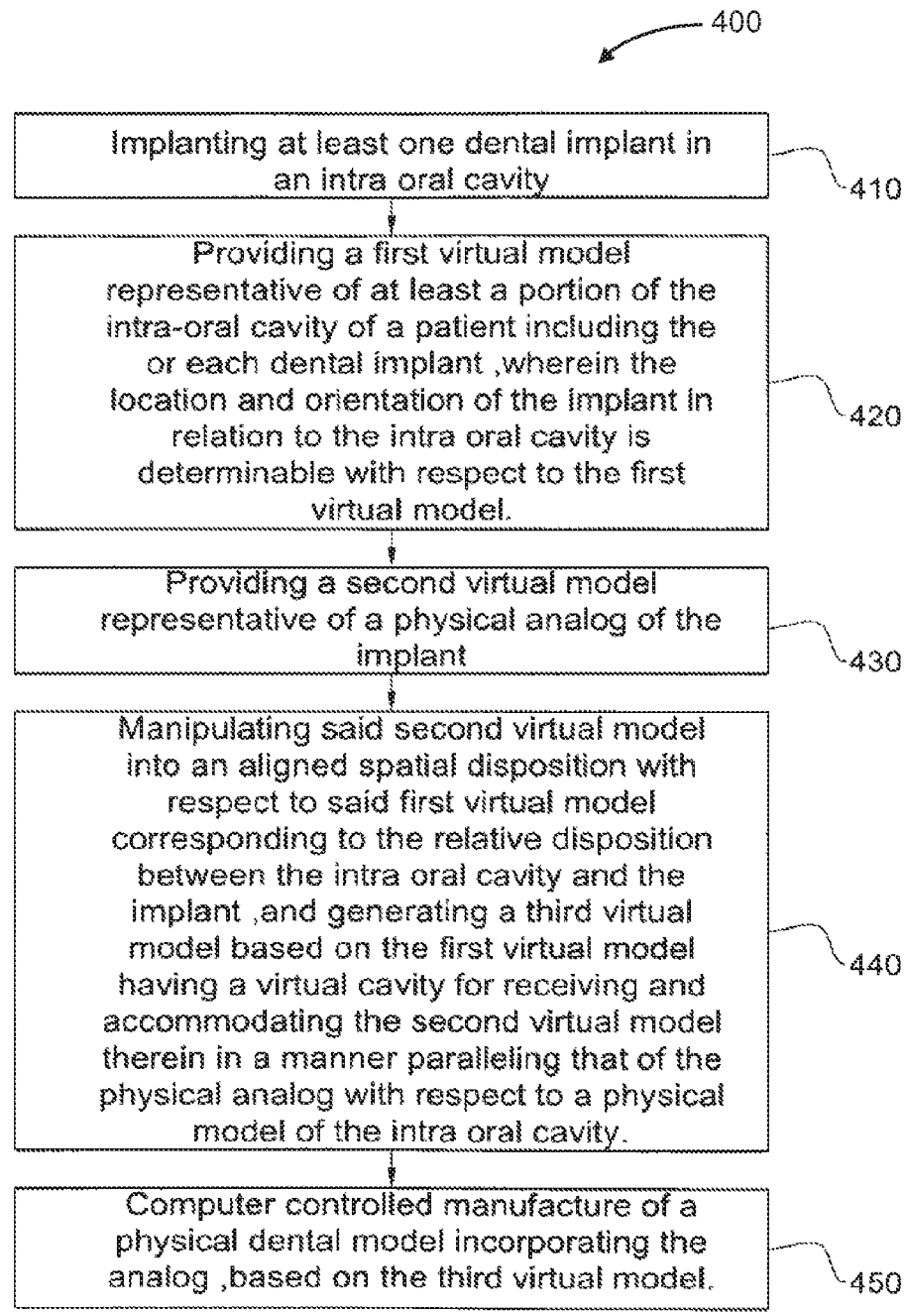
FIG. 2 is a schematic illustration of a method according to embodiments of the invention.

FIG. 2 illustrates a block diagram of a method 400 for use in dental implant procedures according to an embodiment of the invention, and FIG. 1 illustrates the main elements of a system 200 for carrying out the method according to an embodiment of the invention.

While the present description is directed to a single implant, it is readily appreciated that the invention is applicable, mutatis mutandis, to a plurality of implants that may be implanted in the intra oral cavity of a patient, whether the implants are independent from one another, each being used for a separate prosthesis, or whether at least some of the implants are to be coupled to be used together for a single bridge prosthesis or other multiple tooth prostheses, for example.

The system 200 comprises: a first module, including a scanner 250, and a microprocessor or any other suitable computer system 260; a second module comprising a physical analog 230 corresponding to the implant 240 that it is desired to have implanted in the intra oral cavity of a patient, and a manufacturing system 280 for manufacturing a physical model 600 of the intra oral cavity including the analog 230.

The computer system 260 comprises an input interface or module 210 such as a keyboard, mouse, tablet, and so on, an output device or display means or module 220, typically a screen or monitor but may additionally or alternatively include a printer, or any other display system, a processing unit or module 230 such as for example a CPU, and a memory 235.

The scanner 250 is configured for providing surface data of surfaces, in particular hard dental surfaces, other tissue surfaces of the intra oral cavity of a patient, and of the implant 240, in situ or before implantation, and is also operatively connected to the computer system 260 and interacts therewith. The computer system 260 is suitably programmed for reconstructing such surfaces from the surface data provided to provide a first virtual model 500 of the intraoral cavity. Such a scanner may comprise, for example, a probe for determining three dimensional structure by confocal focusing of an array of light beams, for example as marketed under the name of iTero or as disclosed in WO 00/08415, the contents of which are incorporated herein in their entirety. Alternatively, the required scanning may be accomplished using any suitable scanning apparatus for example comprising a hand held probe. Optionally, color data of the intraoral cavity may also provided together with the 3D data, and thus the first virtual model 500 comprises spatial and color information of the dental surfaces scanned. Examples of such scanners are disclosed in US 2006-0001739, and which is assigned to the present Assignee. The contents of the aforesaid co-pending application are incorporated herein by reference in their entirety.

Referring also to FIG. 3(a) to FIG. 3(d), the physical analog 230 comprises a housing 234 having an inner passage or chamber 231, for example including a hexagonal entrance and internally threaded portion, that enables mating with a complementary structure in the permanent abutment, enabling the latter's position with respect to the analog (and thus the physical tooth model) to be dictated in six degrees of freedom. The inner chamber 231 thus corresponds and is nominally identical to the inner chamber 241 of the implant 240. The external form of housing 234 is configured for being embedded in a physical model 600 of the intraoral cavity.

The manufacturing system 280 comprises a computer controlled manufacturing system configured for manufacturing a physical model from a virtual model, with respect to a machine coordinate system C. In this embodiment, the manufacturing process itself is a material removing process such as CNC milling, the physical model 600 incorporating, or being capable of incorporating, the physical analog 230 in the correct spatial orientation and position with respect to the physical model of intraoral cavity corresponding to the spatial orientation and position of the implant 240 in the patient's intra oral cavity.

Referring again to FIG. 2, process 400 broadly includes the following steps:

Step 410—implanting at least one implant 240 in an intra oral cavity of a patient.

Step 420—providing a first virtual model 500 representative of at least a portion of the intra-oral cavity of a patient including the or each dental implant, wherein the location and orientation of the implant in relation to the intra oral cavity is determinable with respect to the first virtual model.

Step 430—providing a second virtual model representative of a physical analog of the implant.

Step 440—manipulating said second virtual model into an aligned spatial disposition, i.e. in spatial registry, with respect to said first virtual model corresponding to the relative disposition between the intraoral cavity and the implant, and generating a third virtual model based on the first virtual model having a virtual cavity for receiving and accommodating the second virtual model therein in a manner paralleling that of the physical analog with respect to a physical model of the intra oral cavity.

Step 450—computer controlled manufacture of a physical dental model 600 incorporating the analog 230, based on the third virtual model.

Referring to each step in turn, step 410 comprises implanting at least one implant in an intra oral cavity of a patient, and follows well-established dental procedures in the art, which will not be described in further detail herein.

Step 420 comprises acquiring an accurate 3D representation, (herein also referred to interchangeably as "three-dimensional model", "3D model", "virtual model" and the like) of the required part of the intraoral cavity of the patient, which forms the focus of the particular implant procedure for a particular patient and regarding which it is desired to obtain the 3D topographical or surface data thereof. The required part may include partial or the full mandibular or maxillary arches, or both arches, and may further include details of the spatial relationship between the two arches in occlusion, and includes the implant in situ in the intra oral cavity.

In any case, this first virtual model 500 may be provided by scanning the intraoral cavity in-vivo using any suitable equipment for scanning a patient's teeth. Such scanning equipment comprises, in this embodiment, the scanner 250 of system 200, though in other embodiments, any other suitable scanner may be used. Alternatively, the 3D digitized data may be obtained in any other suitable manner, including other suitable intra oral scanning techniques, based on optical methods, direct contact methods or any other means, applied directly to the patient's dentition. Alternatively, X-ray based, CT based, MRI based, or any other type of scanning of the patient's intra-oral cavity may be used.

The 3D virtual model is created such as to include sufficient 3D information regarding the implant 240 so that its position with respect to intra oral cavity may be determined in the first virtual model 500. For this purpose it may be sufficient to retain the healing abutment engaged with the implant 240 during scanning, if the engagement position of the healing abutment with respect to the implant 240 is unique and determinable from viewing or scanning at least the exposed part of the healing abutment in the intraoral cavity. Otherwise before the scanning operation, and in the present embodiment, the healing abutment is removed and replaced with an impression abutment 246 (FIG. 3(*a*)) that is shaped, and/or comprises suitable markers or other positional indicators 245 (FIG. 3(*c*)) on the exposed part of the impression abutment 246 in the intraoral cavity, that provide information about the position and orientation of the impression abutment 246, including with respect to the cavity 241 (for example the hexagonal entry configuration in which the permanent abutment is eventually to be seated, in many examples of implants) of the implant 240.

In alternative embodiments, a physical model may be provided of the intraoral cavity, for example via an impression of the intraotral cavity and subsequent casting the impression with plaster, including the implant 240 and the impression abutment 246 (or indeed a suitable healing abutment), and the physical model (or the impression) scanned in any suitable manner to provide the first virtual model 500.

Figure 4A:
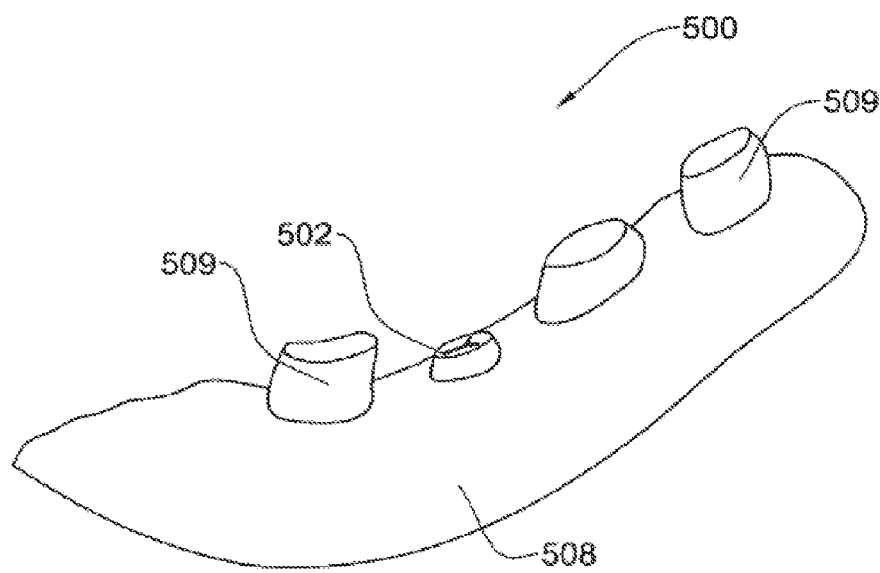
FIGS. 4(a), 4(b) and 4(c) illustrate virtual models respectively of the intraoral cavity, the analog including impression abutment, and of the physical model to be manufactured.
Figure 4B:
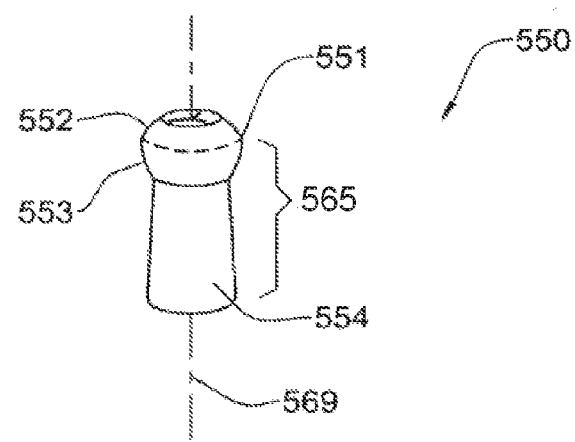
Figure 4C:
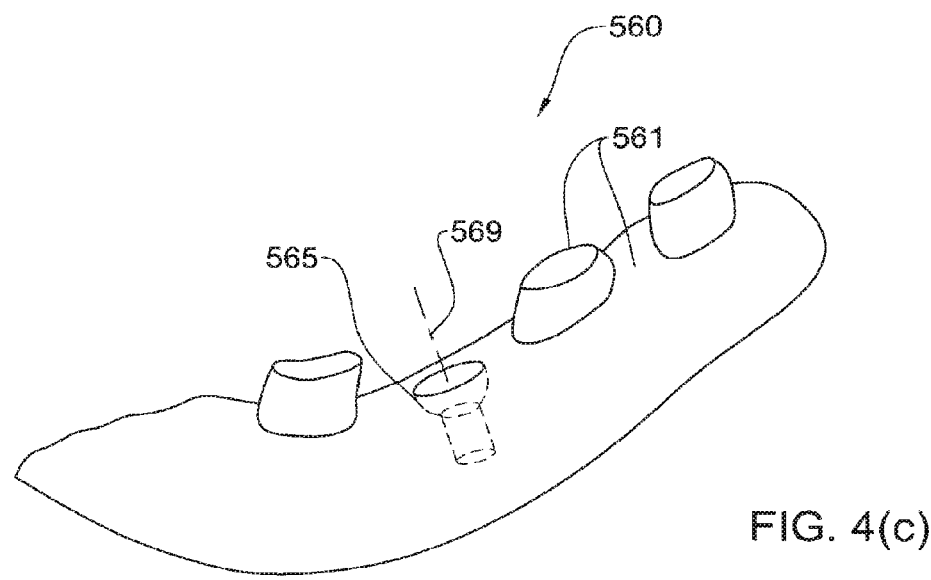

Thus, and referring to FIG. 4(*a*), first virtual model 500 comprises portions 509 corresponding to the real teeth, portions 508 corresponding to the gingival tissues, and a portion 502 corresponding to the exposed part of the impression abutment 246.

In step 430, and referring to FIG. 4(*b*), a second virtual model 550 is provided, comprising a first virtual portion 554 representative of the physical analog 230 of the implant 240, and a second virtual portion 551 representative of the impression abutment 246 coupled thereto.

In the first embodiment, the analog 230 is of constant cross-sectional shape, or alternatively of a tapering cross-sectional shape, such that it is possible to insert the analog in an axial direction into a cavity having a complementary shape. At the same time the cross-section is such (for example oval, asymmetric, polygonal etc) that inserting the analog into a complementary-shaped cavity fixes the position of the analog in the cavity in six degrees of freedom.

In step 440, the second virtual model 550 is manipulated in the virtual environment of the computer system 260 into an aligned spatial disposition with respect to said first virtual model 500, in spatial registry therewith, to generate a third virtual model 560, corresponding to some extent to a virtual combination of said first virtual model and said second virtual model, illustrated in FIG. 4(*c*), in which the second virtual model is essentially "subtracted" from the first virtual model.

The first virtual model 500 and the second virtual model 550 are virtually aligned by manipulating the virtual models by means of the computer system 260 such that the portion 502 corresponding to the exposed part of the impression abutment 246 is brought into registry with a corresponding portion 552 of the second virtual model 550. This may be accomplished in many ways as are known in the art—for example using suitable shape recognition software that compares the shape of one portion at a time of one of the virtual model with different portions of the other virtual model, until a match is found within a particular error threshold. Optionally, the process can be accelerated by user interaction with the computer system 260, wherein the user can identify the general areas of the two virtual models that are common to one another, whereupon the computer system searches for matching the models within the identified areas. Once a match is found, one or both of the models can be rotated and/or translated so as to bring into registry the aligned parts, and thereby aligning the models. Thus aligned, portion 552 (and portion 502) are effectively removed from the first model 500, and a surface 565 is added to the first model to generate the third model 560. Surface 565 comprises the remainder of the first virtual portion 551, i.e. lower portion 553 (corresponding to the part of the outer surface of the impression abutment 246 that is hidden from view), plus the second virtual portion 554. Optionally, surface 565 may be scaled in a radial or lateral direction away from the longitudinal axis 569 of the second virtual model for facilitating a friction fit between the physical model 600 and analog 230.

Virtual model 560 thus comprises an outer virtual surface 561 representative of the dental tissues that are exposed in the intra-oral cavity, and an inner virtual surface 565 representing a cavity for receiving and retaining therein the second virtual model, or at least the part thereof corresponding to the analog, in the same relative position as the implant in the intra oral cavity.

Figure 5:
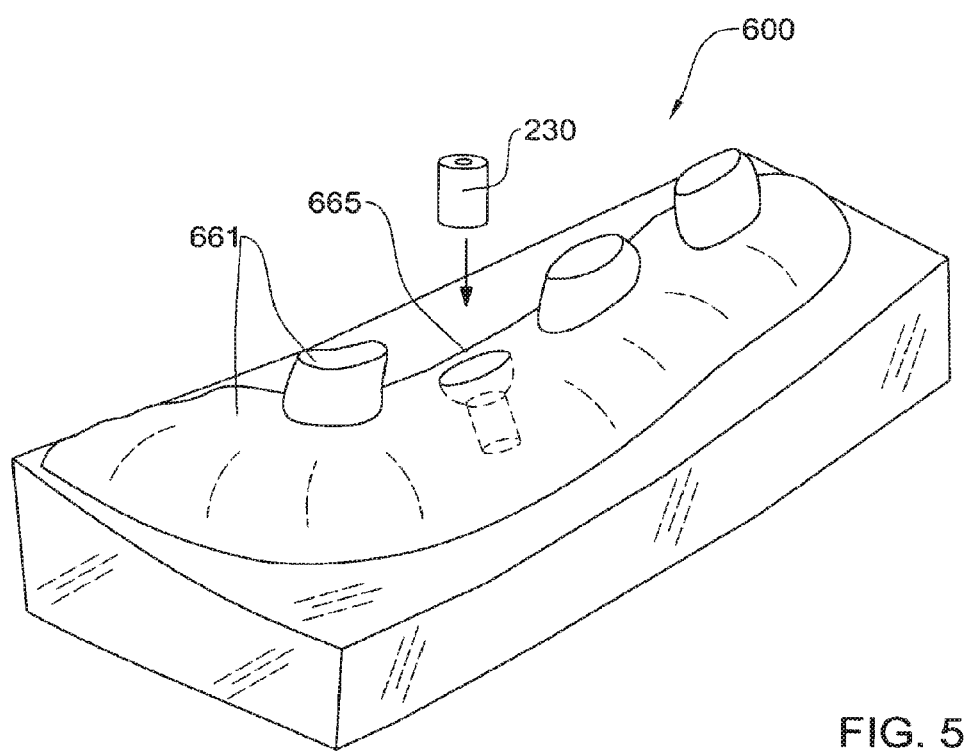
FIG. 5 illustrates in isometric view a physical model corresponding to the virtual model of FIG. 4(c), according to a first embodiment of the invention.

In step 450, and referring to FIG. 5, a physical dental model 600 is manufactured incorporating the analog 230, based on the third virtual model by the manufacturing system 280. In this embodiment, a computer controlled material removing manufacturing process, such as for example CNC milling or machining, is used for milling or otherwise machining the physical model 600 from a blank of material, producing an outer model surface 661 corresponding to surface 561 of the third virtual model 560 and representing dental tissues that are exposed in the intra-oral cavity, and producing a cavity 665 having an internal surface corresponding to surface 565, into which the analog 230 is inserted in a friction fit to assume a position and orientation that is fixed in 6 degrees of freedom with respect to the model 600, corresponding to the position and orientation of the implant 240 in the intraoral cavity of the patient.

Suitable CNC machining paths for producing the external surface 661 and cavity 665 of the model 600 from a blank are generated from the third virtual model 560 in a manner known in the art.

A feature of CNC controlled manufacturing process of the model 600 according to this and other embodiments of the invention is that the machining instructions for producing both, the external surface 661 and cavity 665 of the model 600, are derived from the same virtual model 650 and are thus referenced to the same machine coordinate system C. This enables the same CNC controlled manufacturing system to be used for machining the outer part 661 of the model as well as the cavity 665 of the model, either in parallel or in series, in an accurate and consistent manner, and in one machining operation. Further, there is no need for an intervening scanning operation to determine the 3D shape of the outer surface 661, and then attempt to align the CNC machining of the cavity thereto, as may be required if the outer surface 661 and cavity 665 are manufactured using different methods or which are not based on the same virtual model. The manufacturing process according to the invention is thus also quick and efficient.

The aforesaid computer controlled machining process thus provides a high degree of dimensional accuracy at least in terms of the position and alignment of the cavity 665 with respect to the outer surfaces 661, and thus of analog 230 with respect to the model 600 when mounted therein, as the machining process for both the cavity 665 and surface 661 are based on the same coordinate system.

The physical model 600 thus prepared can assist the dental technician in the design and/or preparation of the permanent abutment, coping, prosthesis and so on, in a manner known in the art.

A system and method according to a second embodiment of the invention comprises all the elements and features of the first embodiment as disclosed herein, mutatis mutandis, with the following differences. In the second embodiment, the analog may not be suitable for, or is unable to be, press-fitted into a cavity in an axial direction. For example the desired analog may be a commercially available analog that may comprise laterally projecting protrusions designed for anchoring the analog in a plaster model when the model is cast using prior art methods with the analog in its properly aligned place by virtue of an impression abutment fixed in the impression material.

Figure 6A:
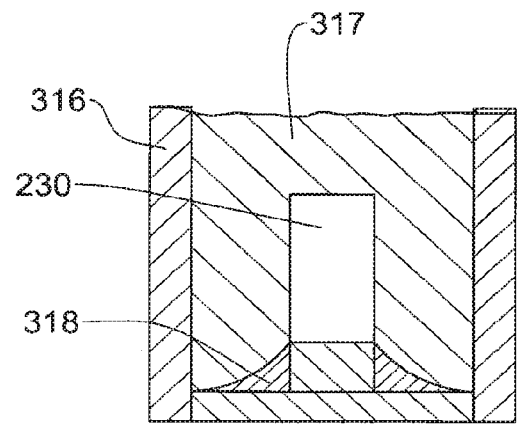
FIG. 6(a) illustrates in cross-sectional side view a casting apparatus for casting a jacketed analog for use with the model of FIG. 6.
Figure 6:
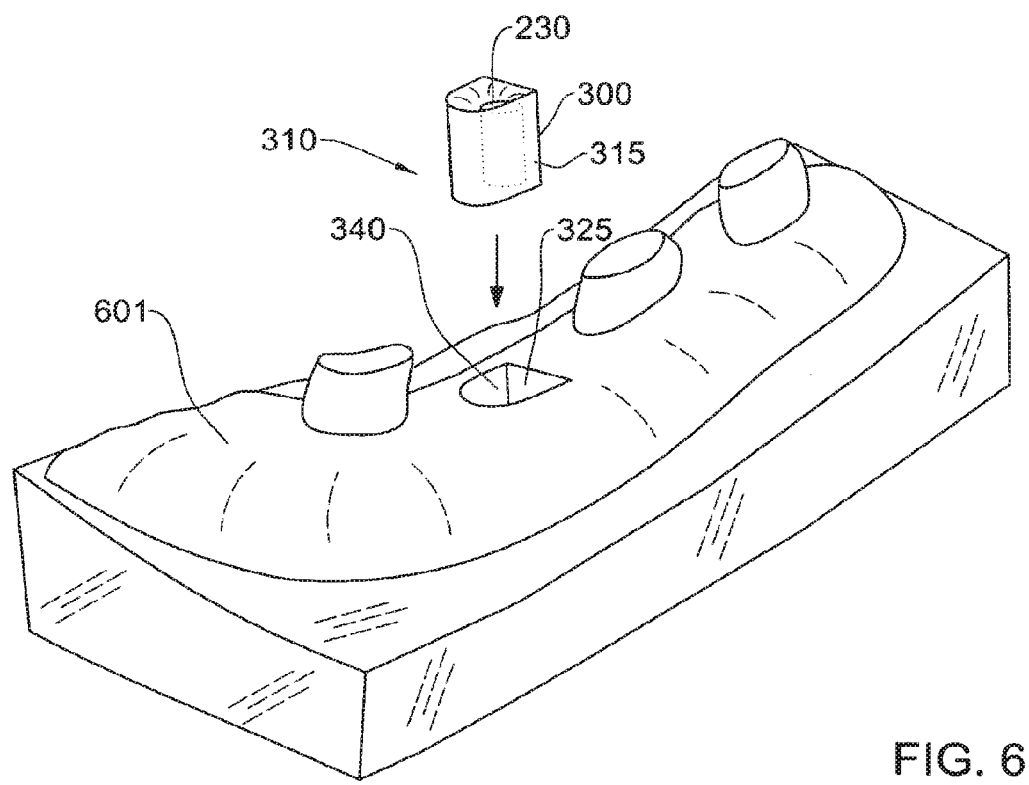
FIG. 6 illustrates in isometric view a physical model according to a second embodiment of the invention.

According to the second embodiment, and referring to FIG. 6, the analog 230 is embedded in a jacket 300 to form a composite analog 310. In this embodiment, the jacket 300 is made from a machinable material, which is milled or otherwise machined in situ on the analog 230 to have an external shape that is readily insertable in a suitable direction, for example an axial direction with respect to the analog 230, in a complementary cavity 340 formed in the physical model, referred to herein by the reference numeral 601. The method steps of FIG. 2 are applicable to the second embodiment, mutatis mutandis, with the main difference that in general at least some of the steps therein relating to the analog 230 and cavity 665, may be applied, in the second embodiment, to the composite analog 310 and cavity 340 instead, mutatis mutandis.

Thus steps 410 and 420 for the second embodiment are substantially the same as for the first embodiment, mutatis mutandis.

In step 430, though, the second virtual model, while representative of the physical analog 230, is further representative of the jacket 300, and thus of the composite analog 310. The shape and relative position of the outer surface 315 of the jacket 300 that is to mate against the internal surface 325 of cavity 340 may be predefined, or may be designed as part of the method of the invention.

According to the first option, the shape and relative position of the outer surface 315 of the jacket 300 that is to mate against the internal surface 325 of cavity 340 may be predefined. The jacket 300 is formed on the analog 230—for example the analog 230 is cast or otherwise embedded in a blank of material, and the jacket 300 is machined until a desired form is provided for outer surface 315. Alternatively, and referring to FIG. 6(a), a cast material 317 may be poured into a precision mold 316 of a predefined internal shape, while analog 230 is being held in a predefined spatial relationship with respect thereto by a jig 318 or the like. In any case, in step 430, the resulting composite analog 310 is scanned, for example, to accurately determine the surface coordinates thereof, while impression attachment is attached to the analog 230, thereby providing a first virtual portion representative of the impression abutment, and a second virtual portion, representative of surface 315. Then, in step 440, the third virtual model is generated in a manner substantially similar to that of the first embodiment, mutatis mutandis, directed to the first and second virtual portions defined in step 430, comprising the outer surfaces corresponding to the exposed surface of the intra oral cavity and a virtual cavity which is substantially complementary to the non-exposed part of the first virtual portion and to the second virtual portion obtained in this embodiment. In the manufacturing step 450, the outer surface and the cavity 340 of the physical model are manufactured in a similar manner to that of the first embodiment, mutatis mutandis, and the composite analog 310 can then be affixed into the cavity 340 in a manner such that the analog 230 is aligned with the model 601 in a manner paralleling the position and orientation of the implant 240 in the intra oral cavity.

Figure 7A:
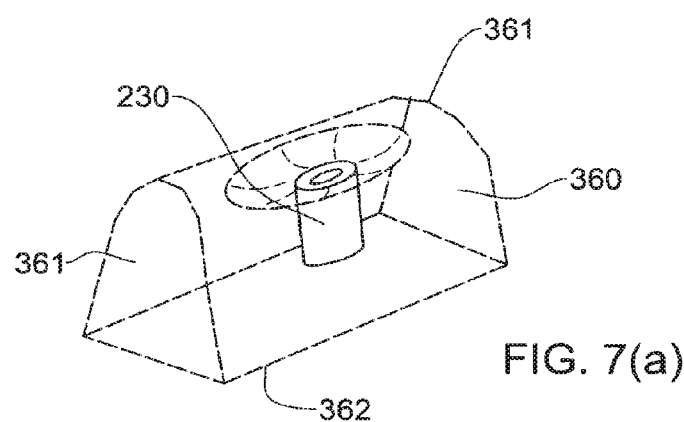
FIG. 7(a) illustrates in isometric view a virtual model of a jacketed analog corresponding to the model of FIG. 7.
Figure 7:
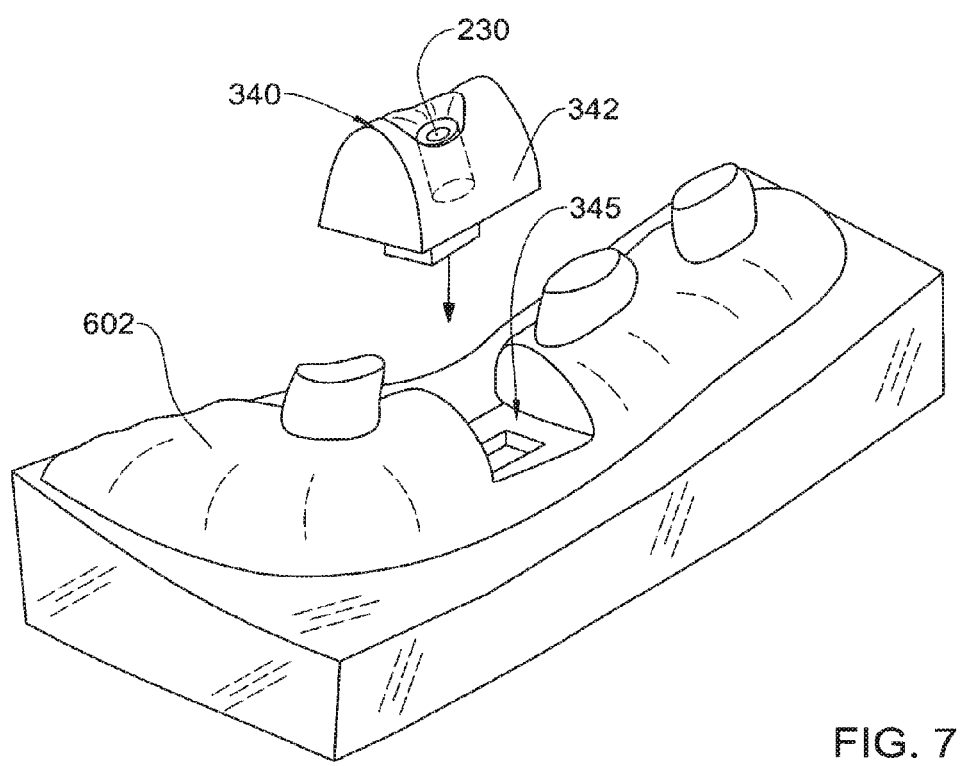
FIG. 7 illustrates in isometric view a physical model according to a variation of the second embodiment of the invention.

According to the second option, the shape and relative position of the outer surface 315 of the jacket 300 that is to mate against the internal surface 325 of cavity 340 is designed as part of the method. Thus, in step 430, the second virtual model representative of the analog 230 is provided in a similar manner to that disclosed herein for the first embodiment mutatis mutandis. This second virtual model is then modified by adding a suitable external virtual surface, outwardly displaced with respect to the virtual surface in a manner that allows for an insertion path to a complementary virtual recess or cavity provided in the third virtual model. For example, the aforesaid external virtual surface may comprise a generally prismatic form, for example corresponding to that of the external surface 315 illustrated in FIG. 6. Alternatively, and referring to FIGS. 7 and 7(a), for example, the external virtual surface, marked at 360, may correspond to part of the first virtual model and is representative of an exposed part of the outer surface of the buccal and labial gingival tissues close to the position of the implant 240 in the intra oral cavity, and further include virtual side portions 361 and base 362 to enclose the initial virtual model of the analog in a virtual volume. In step 440, the third virtual model is generated from the first virtual model by effectively removing a virtual surface corresponding to surface 360 of the second virtual model, and adding virtual surfaces complementary to side portions 361 and base 362 to form a virtual recess or cavity configured for enabling the second virtual model to fit therein. In step 450, the physical model 602 is manufactured in a similar manner to that in the first embodiment, mutatis mutandis, producing a recess or cavity 345 as well as the external surfaces corresponding to parts of the intra oral cavity. Step 450 also comprises manufacturing the composite analog 340, based on the modified second virtual model generated in step 430, and this may be done, for example, by casting or otherwise embedding the normally hidden parts of the analog 230 in a blank of material, and the jacket 342 is then CNC machined based the second virtual model, in which the analog is held in a known position with respect to the manufacturing system 280.

A system and method according to a third embodiment of the invention comprises all the elements and features of the first and second embodiments as disclosed herein, mutatis mutandis, with the following differences. In the third embodiment, the analog is not press-fitted in place with respect to the physical model—for example, the analog may not be suitable for, or is unable to be, press-fitted into a cavity in an axial direction.

Figure 8:
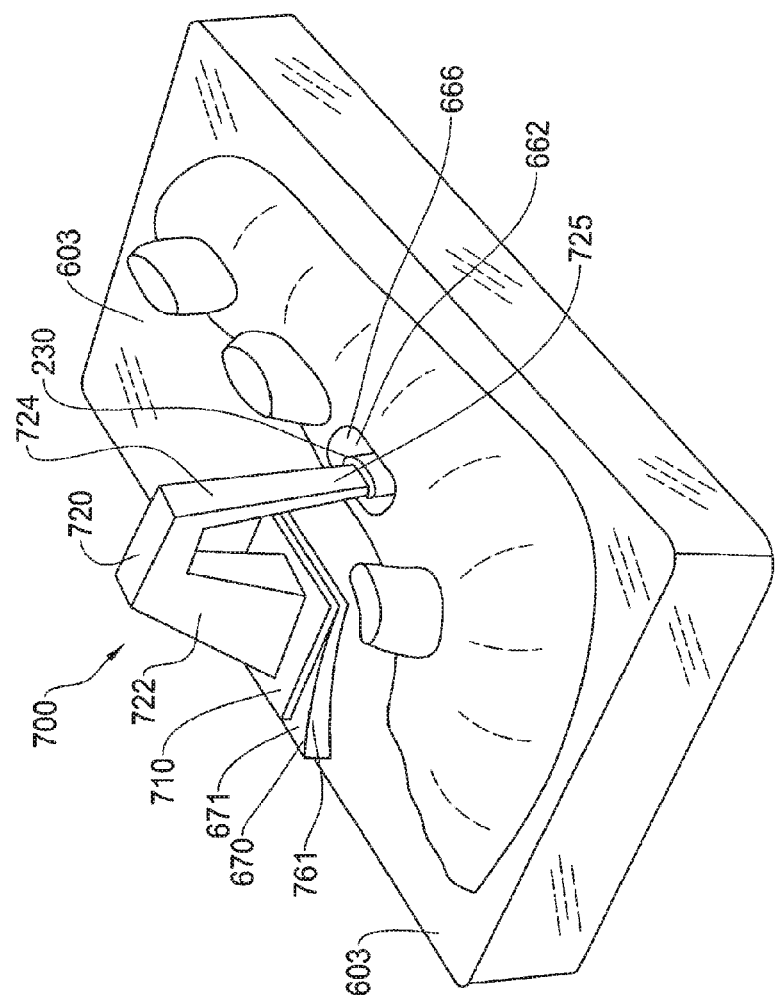
FIG. 8 illustrates in isometric view a physical model according to a third embodiment of the invention, including a positioning jig for use therewith.

According to the third embodiment, and referring to FIG. 8, a physical model 603 of the intra oral cavity is manufactured in a similar manner to that disclosed herein for the first embodiment, mutatis mutandis, with two main differences. The first difference is that the machined cavity 666 is significantly larger than required for accommodating the analog 230 in a tight fit, and the cavity may be of any desired shape so long as the analog may be inserted therein, with a clearance 662, in the position and orientation with the respect to the model 603 that parallels the position and orientation of the implant 240 in the intra oral cavity. For example, in step 440 it may only be necessary to establish the spatial relationship between the second virtual model and the first virtual model, but thereafter the virtual cavity corresponding to cavity 666 may be created by effectively removing a "slice" of the first virtual model that is bounded by the location of the two adjacent teeth in the model: The second difference is that the third virtual model is created to include a virtual representation of an integral mating platform 670, which is then integrally manufactured with the physical model 603.

According to another aspect of the invention, a jig is also provided for the third embodiment of the system and method of the invention, for holding the analog 230 within the cavity 666 in the desired position and orientation therein until a filling and fixing material, for example epoxy resin, is placed in the clearance gap 662 and allowed to set, cementing the analog in place, after which the jig can be disengaged from the analog 230 and from the model 603.

The jig 700, according to a first embodiment, comprises a base 710, and a substantially rigid, inverted U-shaped strut 720, having one arm 722 rigidly attached to the base 710 and a second arm 724 having a free end 725 onto which an analog 230 may be mounted at the abutment receiving end thereof in a known and unique spatial relationship with respect thereto. There is thus a unique and fixed spatial relationship between the end 725 and the base 710. The shape of the jig is only illustrative, and any suitable arrangement may be used that has a fixed geometrical relationship between the model-engaging base and the analog engaging end. Furthermore, the mating platform 670 is remote from parts of the model representing dental surfaces, and thus facilitates the cementing procedure for the user as there is a minimum or zero obfuscation of the cavity 666 and analog 230 by the jig.

Figure 9:
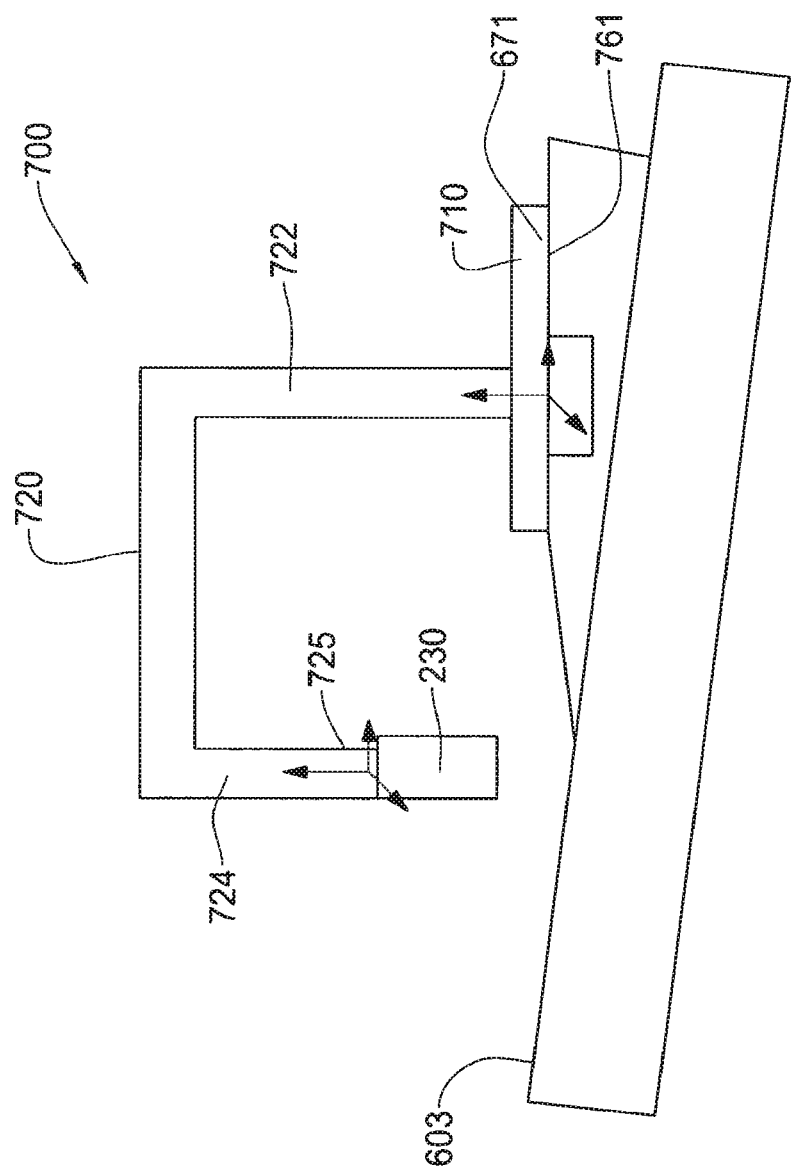
FIG. 9 illustrates in side view a variation of the jig of FIG. 8.

Referring also to FIG. 9, the jig 700 is mounted to the model 602 by engaging the mutually abutting surfaces of base 710 and the mating platform 670 in a unique mating position, and is thus engaged in a fixed position therein until removed. In this embodiment, the geometry of the jig 700 is predefined—for example the jig 700 may be a previously manufactured off the shelf item—and the position and orientation of the mating platform 670 with respect to the cavity 666 is designed such that when the jig 700 is properly engaged with the model 603, with the base 710 firmly seated in position on the mating platform 670, the end 725 automatically brings the analog 230 attached thereto into its correct position with respect to the cavity 666, and thus the model 603. Thus the model 603 may be manufactured having an extended base portion 605, if necessary, such as to provide the required position and orientation to the base 710 via the mating platform 670.

The corresponding position and orientation of the mating platform 670 can be calculated in step 440 in a relatively straightforward manner. Having already designed the virtual equivalent of the cavity 666 in step 440, the required position and orientation of the second virtual model representing the analog 230 is also known. The relative spatial position between the end 725 and the base 710 of the jig 700 is also known, and thus by effectively fixing the end 725 to be in an engagement position, in a virtual sense, with the virtual model of the analog 230, the corresponding position of the base 710 with respect to the third virtual model is automatically fixed. Accordingly, the shape and position of the virtual equivalent of the mating platform 670, in particular the abutting surface 671 thereof, is readily defined in the third virtual model, being essentially complementary to the abutting surface 761 of the base 710, which thus enables the physical model 603 to be manufactured integrally with the mating platform 670 in place.

It is to be noted that rather than a single jig 700, there may optionally be provided a family of predefined jigs, each having the same general properties of jig 700, but each having a different fixed geometrical relationship between the respective end 725 and base 710 thereof. Thus, in step 440, the computer system 260 may determine automatically, or via interaction with the user, which of the particular jigs provides an optimum design for the model 603 for use therewith.

Additionally or alternatively, one or more such jigs may be made from several rigidly connectable modular components, and the user (or computer system 260) may choose between the available components to build an optimum jig, on the basis of which the platform 670 is designed and manufactured.

Figure 10:
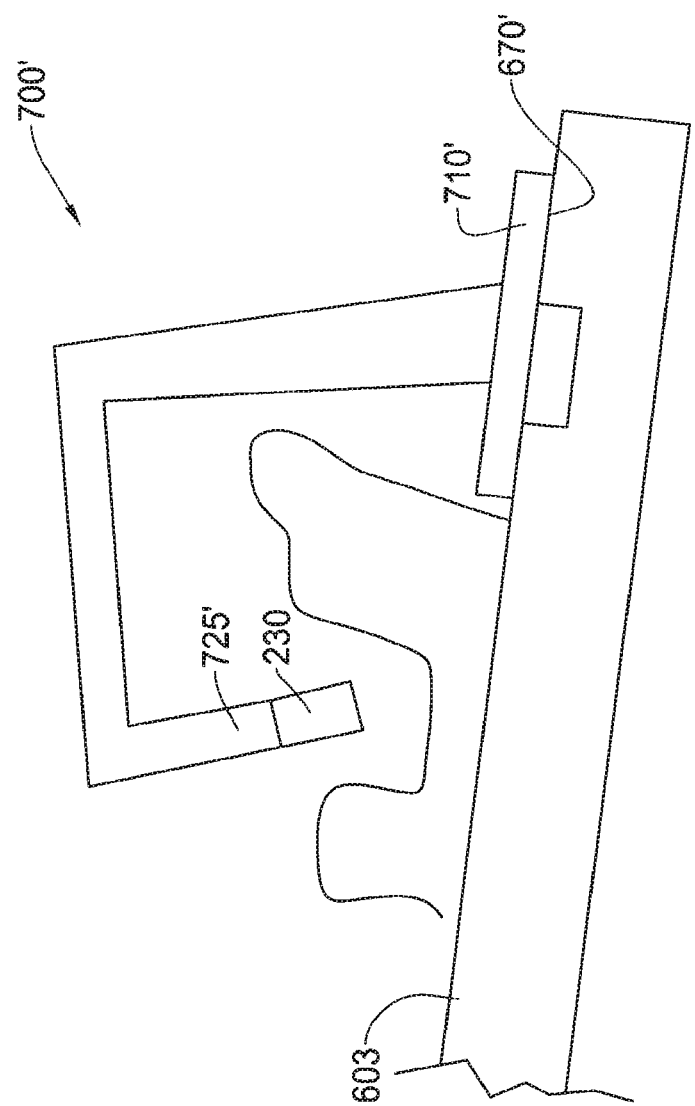
FIG. 10 illustrates in side view another embodiment of the jig.

In a variation of the third embodiment, and referring to FIG. 10, a second embodiment of the jig, designated with the reference numeral 700', comprises all the elements and features of the first embodiment of the jig as disclosed herein, mutatis mutandis, with the following differences. In the second jig embodiment, the jig 700' may be specially designed and manufactured for use with a particular model 603. In such a case, the jig 700' may have the same general properties and characteristics of jig 700, but the particular geometrical relationship between the end 725' and base 710' thereof is optimized in any desired manner, with the constraint that the base 710 is to be mounted at a fixed position and orientation on the model 603 to a standard mating platform 670'.

Figure 11:
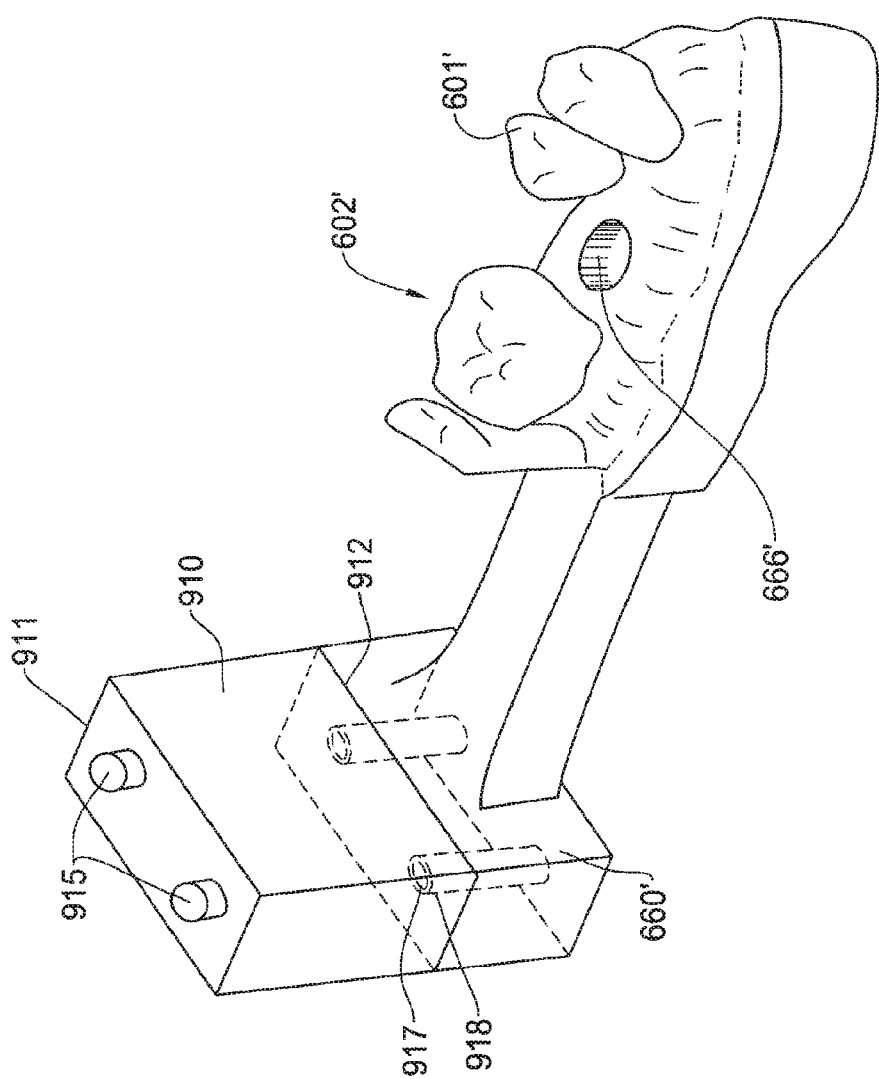
FIG. 11 illustrates in isometric view a physical model according to the third embodiment of the invention, including a spacer member of a positioning jig for use therewith.
Figure 12:
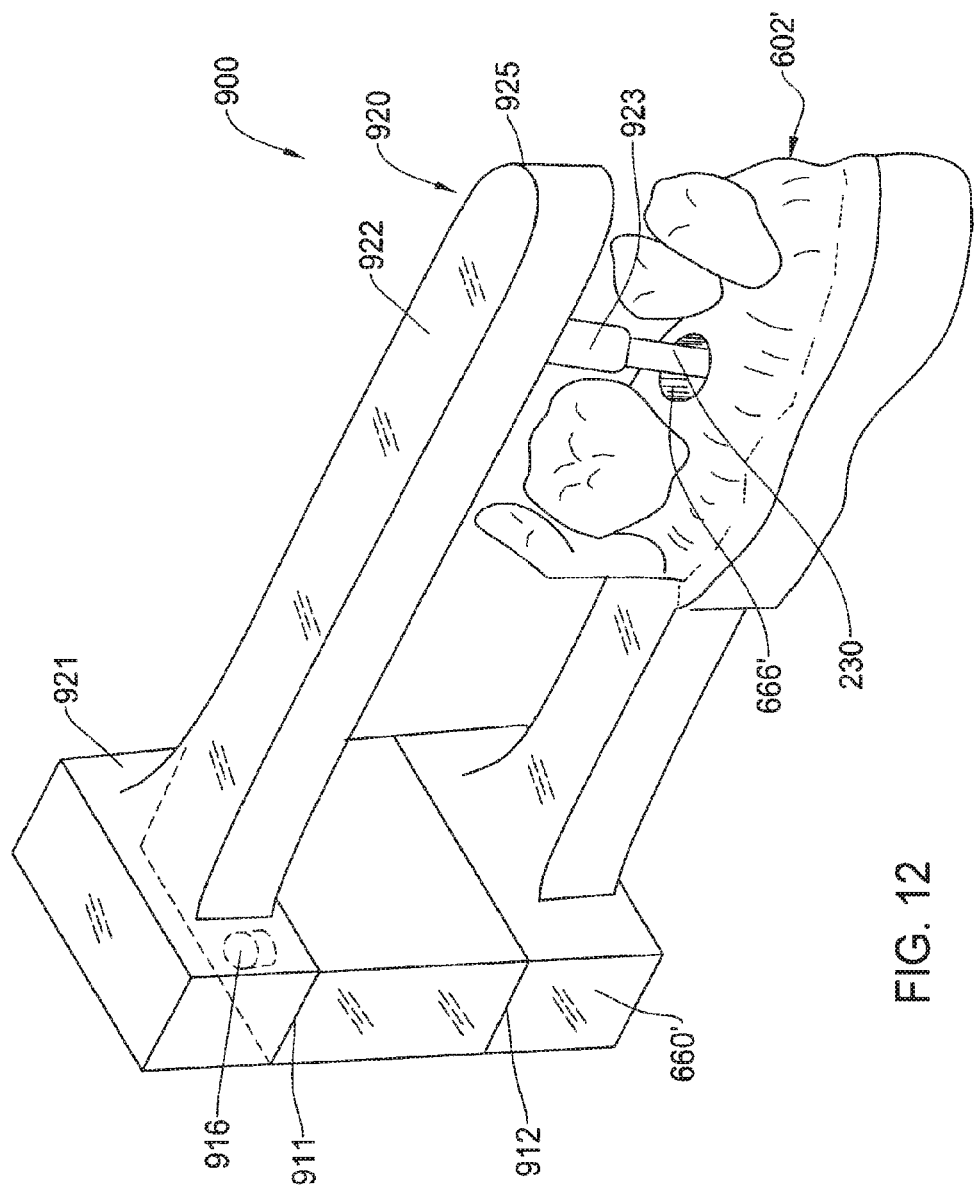
FIG. 12 illustrates in isometric view the physical model of FIG. 11, including a positioning jig for use therewith.
Figure 13:
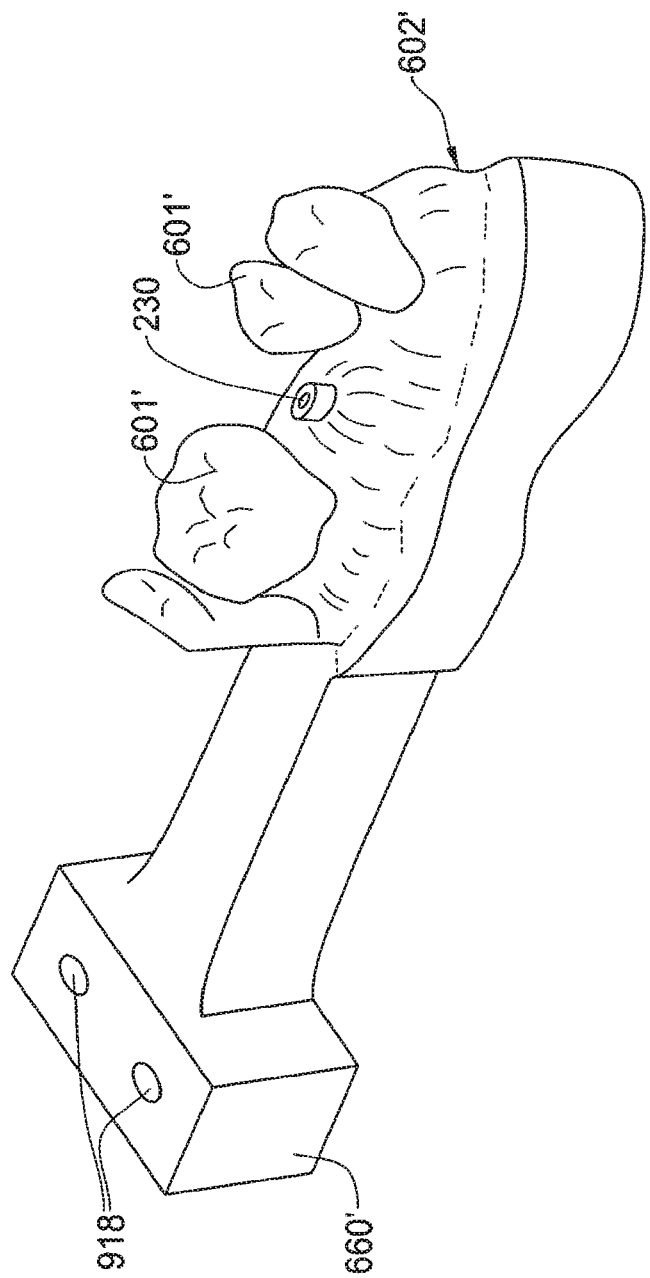
FIG. 13 illustrates in isometric view the physical model of FIGS. 11 and 12, with the analog fixed in place.

Referring to FIGS. 11 to 13, a third embodiment of the jig, designated with the reference numeral 900, comprises all the elements and features of the first and second embodiments of the jig as disclosed herein, mutatis mutandis, with the following differences. In the third jig embodiment, the jig 900 comprises a substantially rigid strut 920, comprising a spacer member 910 and an arm 922 rigidly attachable to the spacer member 910 at one end 921 of the arm 922. At another end 925 of arm 922 a mounting arrangement 923 is provided, onto which an analog 230 may be mounted at the abutment receiving end thereof in a known and unique spatial relationship with respect thereto. There is thus a unique and fixed spatial relationship between the end 925 and mounting arrangement 923, and the spacer member 910.

Spacer member 910 comprises two longitudinally opposed free ends 911, 912 thereof, and is reversibly attached to end 921 of arm 922 to form L-shaped strut 920 by an engagement arrangement, including a pair of laterally-spaced pins 915 projecting from end 911 and complementary sockets or apertures 916 formed in the end 921 to receive and retain the pins 915. The mating faces between the ends 921 and 911 and the pins 915 and apertures 916 effectively fix the relative spatial disposition between the arm 922 and the spacer member 910 in six degrees of freedom. In alternative variations of this embodiment, any other suitable engagement or mounting arrangement may be used to ensure that the arm 922 and spacer member 910 are connected to one another in spatially fixed manner with respect to one another, which is reversible and repeatable.

At the same time, the tooth model, 602' comprises a base portion 660' onto which jig 900 may be mounted via the spacer member 910, wherein end 912 is reversibly attached base portion 660' by another engagement arrangement, including a pair of laterally-spaced pins 917 projecting from end 912 and complementary sockets or apertures 918 formed in base portion 660' to receive and retain the pins 917. The mating faces between the end 912 and base portion 660' and the pins 917 and apertures 918 effectively fix the relative spatial disposition between base portion 660' and the spacer member 910 in six degrees of freedom. In alternative variations of this embodiment, any other suitable engagement or mounting arrangement may be used to ensure that the base portion 660' and spacer member 910 are connected to one another in spatially fixed manner with respect to one another, which is reversible and repeatable.

In this embodiment, the geometry of the spacer member 910 is predefined—for example the spacer member 910 may be a previously manufactured off the shelf item and the position and orientation of the base portion 660' with respect to the cavity 666', and the geometry of the arm 922 and relative position between the ends 921, 922 thereof, are designed such that when the jig 900 is properly engaged with the model 602', with the spacer member 910 firmly seated in position on the base portion 660', and the arm 922 firmly engaged to the spacer member 910, the end 925 automatically brings the analog 230 attached thereto into its correct position with respect to the cavity 666', and thus the model 602'.

For example, the model 602' may be manufactured having base portion 660' in a particular standard form and position with respect to the model dentition 601' (i.e., the parts of the model that have external surfaces representative of the external surfaces of the real teeth), and the form and dimensions of the spacer member 910 can also be standard or chosen from a set of standard sizes/forms.

The corresponding position and orientation of the base portion 660' can be calculated in step 440 in a relatively straightforward manner. Having already designed the virtual equivalent of the cavity 666' in step 440, the required position and orientation of the second virtual model representing the analog 230 is also known. The relative spatial position between the end 925 (and mounting arrangement 923) and the spacer member 910 of the jig 900 is also known, and thus by effectively fixing the end 925 to be in an engagement position, in a virtual sense, with the virtual model of the analog 230, the corresponding position of the end 912 of the spacer member 910 with respect to the third virtual model is automatically fixed. Accordingly, the shape and position of the virtual equivalent of the arm 922, in particular the end 925 and end 921 thereof, may be readily defined in the third virtual model, being essentially such as to position the virtual model of the analog in the desired spatial disposition with respect to the corresponding position of the end 912 of the spacer member 910.

A suitable machining or other material removal operation may be used for manufacturing the arm 922 from a blank, or alternatively the arm 922 may be formed via a rapid prototyping process. Mounting arrangement 923 may be integrally formed with the arm 922, or alternatively may be formed separately and fixed in place at end 925 is the required spatial disposition with respect thereto.

Once the analog 230 is held in place with respect to the cavity 666' via jig 900, it is cemented in place using any suitable cement, adhesive and/or filler, after which the jig may be removed. Thereafter (as with other embodiments of the physical dental model), the dental model may be used for designing and fitting a prosthesis to the analog 230, which facilitates the ultimate engagement of the prosthesis with the respective implant in the intra-oral cavity of the patient. To further aid in this process, it may be desired to mount the model 602' in an articulator, and thus, the base portion 660' and the engagement arrangement thereof, in particular the apertures 918, may be designed in the first place also to be compatible with the mounting arrangement of an articulator, which for example may have mounting pins similar to pins 917. A physical model of the patient's opposed dentition in occlusal relationship with the teeth that are represented by model 602' can also be mounted to the articulator, and thus the user can study the occlusal relationship between the two dental models and the effect of the prosthesis.

It is to be noted that the jig according to the present invention may be used with any suitable cavity, which can be of any suitable shape and is larger than the part of the physical analog that it is desired to embed therein, such as to provide a clearance gap between this part of the analog and the cavity. Thus, the term "cavity" refers to any well, bore, slot or any other receiving volume created in the physical model in which the analog may be accommodated and cemented in place by means of suitable filler material applied to the clearance gap.

Figure 14:
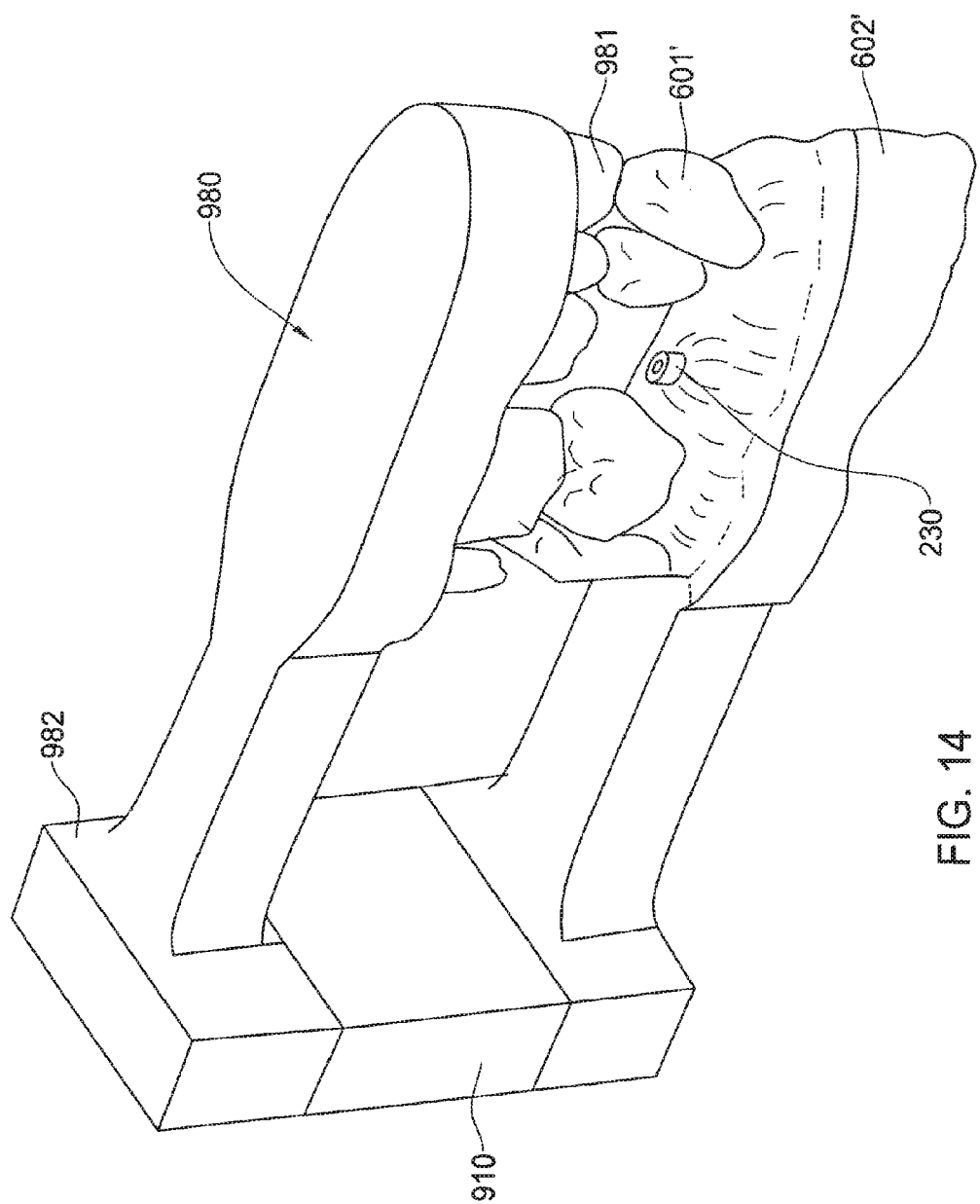
FIG. 14 illustrates in isometric view the physical model of FIG. 13, including the spacer member of FIG. 11, and an auxiliary dental model of an opposed dentition, in occlusal relationship.

Alternatively, and as illustrated in FIG. 14, a physical model 980 of the patient's dentition of the opposed dental arch in occlusal relationship with the teeth 601' can be mounted to the spacer member 910 once the arm 922 is removed, and thus the user can study the occlusal relationship between the two dental models and how this is affected by the prosthesis that is mounted to the implant (not shown). For this purpose, the form and size of the spacer member 910, as well as the size and form of the engaging base portion 982 of the dental model 980 are such that when the dental models 982, 602' are mounted to one another via the spacer member 910, the corresponding teeth models 981, 601' are in occlusal relationship.

A system and method according to a fourth embodiment of the invention comprises all the elements and features of the first through third embodiments as disclosed herein, mutatis mutandis, with the following differences. In the fourth embodiment, the analog is not assembled into the manufactured physical model, but rather the physical model is integrally manufactured with the analog.

According to the fourth embodiment, steps 410 to 440 can be substantially identical to the same steps as disclosed for the first embodiment, mutatis mutandis.

However, and referring to FIG. 15, the manufacturing step 450 comprises embedding the analog 230 in a blank 800 of material in a position and orientation that enables the physical model 606 to be machined from the blank 800 such that at the end of the machining or material removal process, the analog 230 will effectively end up in the desired position vis-a-vis the finished model 606. Thus the starting point of the blank 800 may be such that the analog is effectively fully submerged in the blank 800, in a known position and orientation with respect to a reference plane P of the blank. For example, the analog 230 may be held in a particular, known, position and orientation with respect to a plate 820 via a rigid, though optionally removable jig 840. Plate 820 defines plane P at the upper surface 821 thereof. The blank 800 can be formed by casting a suitable machinable material over plate 820 (contained by a suitable surrounding wall, not shown) up to a level above the analog 230 sufficient to ensure that the heights of all parts of the eventual model 606 are below this level. For this purpose, step 440 may further comprise the step of constructing a virtual blank surrounding the third virtual model, and comprising a reference plane corresponding to plane P in the corresponding position with respect to the relative position of the second virtual model re the third virtual model, to that of the relative position and orientation between the analog 230 and plate 820, as provided by the jig 840. This facilitates design and manufacture of the blank 800.

Once the blank 800 is ready, it can be positioned in the manufacturing system 280, calibrated to identify the position and orientation of the analog 230 and plane P with respect to its coordinate system C. For this purpose, plate 820 may optionally be configured for being mountable with respect to the manufacturing system 280 in a predetermined and unique manner relative to the coordinate system C thereof, for example, and thus when mounted for machining in the manufacturing system 280 the position and orientation of the analog 230 with respect to the plate 820, and thus the manufacturing system's coordinate system is automatically fixed, thereby automatically aligning the blank in the manufacturing system 280, which can then mill or otherwise machine the blank 800 to produce the model 606 therefrom.

It is to be noted that the computer system 260 in which the virtual models are created and manipulated according to any of the embodiments of the invention does not necessarily need to be located in the same geographical location as the scanner 250 and patient. Thus, while the scanning of the patient is usually done at a dental clinic by the dentist or other dental practitioner, the dental clinic may instead or additionally be linked to one or more dental labs, and possibly also to a dental service center via a communication means or network such as for example the Internet or other suitable communications medium such as an intranet, local access network, public switched telephone network, cable network, satellite communication system, and the like. Additionally or alternatively, the communication means may include postal or courier services, the data being communicated via a transportable medium such as an optical disc, magnetic disc and so on. In any case, once the third virtual model is created, the physical dental model, and other dental procedures not carried out on the actual patient, may be carried out by the dental lab which receives the required data generated by the method 400 via the communications means. The dental service center may be used for manufacturing dental hardware that requires a very high degree of precision, for example inner surfaces of prostheses that are required to match external surfaces of copings, and possibly also the copings themselves.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

What is claimed is:

1. A system for manufacturing a physical dental model of an intra-oral cavity, comprising:
    a computer system configured for providing a first virtual model representative of at least a part of the intra-oral cavity including at least one dental implant implanted therein, said first virtual model comprising a virtual portion representative of a respective physical portion of a said at least one dental implant, said virtual portion being at a virtual spatial disposition with respect to said first virtual model, and for providing an implant spatial disposition of the said at least one dental implant with respect to said part of the intra oral cavity based on said virtual spatial disposition;
    a physical analog corresponding to said at least one dental implant; and
    a manufacturing system configured for manufacturing the physical dental model, corresponding to said part of the intra-oral cavity, based on said first virtual model, said physical dental model including a physical analog corresponding to said at least one dental implant, said physical analog being at an analog spatial disposition with respect to said physical dental model corresponding to said implant spatial disposition of said at least one dental implant with respect to said part of the intra oral cavity provided by said computer system, the manufacturing system configured for manufacturing the physical analog embedded in a jacket structure by applying a layer of material on the physical analog and machining the layer of material such that the jacket structure is shaped to removably couple to a cavity structure formed in the physical dental model.

2. The system according to claim 1, further comprising scanning apparatus configured for providing surface data to said computer system for providing said first virtual model.

3. The system according to claim 1, wherein said manufacturing system is computer controlled.

4. The system according to claim 1, wherein said manufacturing system is configured for manufacturing said physical dental model via a material removal operation applied to a blank of material.

5. The system according to claim 1, wherein said manufacturing system is configured for manufacturing said physical dental model via a CNC machining operation applied to a blank of material.

6. The system according to claim 1, wherein said manufacturing system is configured for manufacturing said physical dental model via a rapid prototyping process.

7. The system according to claim 1, wherein:
    said computer system is configured to provide a second virtual model at least partially representative of said physical analog, and generate a third virtual model including a virtual cavity configured for virtually accommodating the second virtual model therein; and
    wherein said manufacturing system is configured to manufacture said physical dental model further based on said third virtual model.

8. The system according to claim 7, wherein said computer system is configured to generate said third virtual model by manipulating said second virtual model into an aligned virtual spatial disposition consistent with the said virtual spatial disposition and corresponding to said implant spatial disposition of the respective dental implant with respect to said part of the intra oral cavity.

9. The system according to claim 7, wherein said manufacturing system is configured to form an outer physical dental model surface corresponding to dental surfaces of said part of the intra oral cavity, and to form a physical recess in said physical dental model for accommodating said physical analog at said analog spatial disposition, said physical recess corresponding to said virtual cavity.

10. The system according to claim 9, wherein said virtual cavity has a virtual form corresponding to a physical form that is complementary to that of the respective said physical analog, such that said physical recess formed in said physical dental model provides a fit with respect to said physical analog to accommodate the respective said physical analog therein at said analog spatial disposition.

\* \* \* \* \*